(12) United States Patent
Foss et al.

(10) Patent No.: US 9,908,987 B2
(45) Date of Patent: Mar. 6, 2018

(54) ANTIMICROBIAL AND ANTIFUNGAL POLYMER FIBERS, FABRICS, AND METHODS OF MANUFACTURE THEREOF

(71) Applicant: PurThread Technologies, Inc., Cary, NC (US)

(72) Inventors: Stephen W. Foss, Naples, FL (US); Stanley Chamberlain, Chapel Hill, NC (US); Lloyd Frick, Chapel Hill, NC (US)

(73) Assignee: PurThread Technologies, Inc., Cary, NC (US)

( * ) Notice: Subject to any disclaimer, the term of this patent is extended or adjusted under 35 U.S.C. 154(b) by 753 days.

(21) Appl. No.: 14/457,546

(22) Filed: Aug. 12, 2014

(65) Prior Publication Data

US 2015/0044449 A1 Feb. 12, 2015

Related U.S. Application Data

(60) Provisional application No. 61/864,957, filed on Aug. 12, 2013.

(51) Int. Cl.
| | |
|---|---|
| C08K 9/00 | (2006.01) |
| C08K 3/22 | (2006.01) |
| C08K 3/30 | (2006.01) |
| D01G 13/00 | (2006.01) |

(52) U.S. Cl.
CPC ............. *C08K 3/22* (2013.01); *C08K 3/30* (2013.01); *D01G 13/00* (2013.01); *C08K 2003/2241* (2013.01); *C08K 2003/3045* (2013.01); *C08K 2201/013* (2013.01); *D10B 2331/04* (2013.01); *Y10T 428/249921* (2015.04)

(58) Field of Classification Search
CPC ............. C08K 3/22; C08K 3/30; B05D 1/005
See application file for complete search history.

(56) References Cited

U.S. PATENT DOCUMENTS

| | | | |
|---|---|---|---|
| 4,578,414 A | 3/1986 | Sawyer et al. | |
| 4,786,556 A | 11/1988 | Hu et al. | |
| 4,891,391 A | 1/1990 | McEntee | |
| 5,064,599 A * | 11/1991 | Ando | A01N 25/34 |
| | | | 162/157.2 |
| 5,405,644 A | 4/1995 | Ohsumi et al. | |
| 6,384,168 B1 | 5/2002 | Tanaka et al. | |
| 6,723,428 B1 | 4/2004 | Foss et al. | |
| 6,841,244 B2 | 1/2005 | Foss et al. | |
| 6,946,196 B2 | 9/2005 | Foss | |
| 8,183,167 B1 | 5/2012 | Delattre et al. | |
| 8,193,267 B2 | 6/2012 | Burton et al. | |
| 2003/0204916 A1 | 11/2003 | Green et al. | |
| 2004/0018359 A1 | 1/2004 | Haggquist | |
| 2004/0096654 A1 | 5/2004 | Morin et al. | |
| 2004/0180200 A1 | 9/2004 | Bertamini et al. | |
| 2004/0259973 A1 | 12/2004 | Sakuma et al. | |
| 2005/0028563 A1 | 2/2005 | Mullins et al. | |
| 2005/0054830 A1 | 3/2005 | Islam et al. | |
| 2005/0245685 A1 | 11/2005 | Otake et al. | |
| 2006/0074154 A1 | 4/2006 | Harashina et al. | |
| 2006/0142438 A1 | 6/2006 | Ishii et al. | |
| 2006/0246149 A1 | 11/2006 | Buchholz et al. | |
| 2006/0252326 A1 | 11/2006 | Mishler | |
| 2008/0009586 A1 | 1/2008 | VanSumeren et al. | |
| 2008/0063679 A1 | 3/2008 | Sawalfta et al. | |
| 2008/0090945 A1 | 4/2008 | Langrick et al. | |
| 2008/0187603 A1 | 8/2008 | Sawafta | |
| 2008/0197528 A1 | 8/2008 | Wood | |
| 2008/0242794 A1 | 10/2008 | Sandford et al. | |
| 2008/0268011 A1 | 10/2008 | Goldmann et al. | |
| 2008/0306181 A1 | 12/2008 | Garey et al. | |
| 2009/0068283 A1 | 3/2009 | Sugiura et al. | |
| 2009/0130161 A1 | 5/2009 | Sarangapani | |
| 2009/0218266 A1 | 9/2009 | Sawafta et al. | |
| 2009/0246258 A1 | 10/2009 | Shukla et al. | |
| 2009/0269379 A1 | 10/2009 | Herbst | |

(Continued)

FOREIGN PATENT DOCUMENTS

| | | |
|---|---|---|
| CN | 101705527 A | 5/2010 |
| EP | 2655709 A2 | 10/2013 |

(Continued)

OTHER PUBLICATIONS

"International Preliminary Report on Patentability" under Chapter 1 of the Patent Cooperation Treaty, in International Application No. PCT/US2014/050666, dated Feb. 16, 2016 (7 pages).

Czarnobaj, K. Sol-gel-processed silica/polydimethylsiloxane/calcium xerogels as polymeric matrices for Metronidazole delivery system. Polym. Bull. 66:223-237 (2011) (15 pages).

"International Search Report" and "Written Opinion" of PCT Application No. PCT/US2014/050666, dated Jan. 22, 2015 (10 pages).

"European Search Report" for European Application No. 11850293.9, dated Apr. 16, 2014 (7 pages).

(Continued)

*Primary Examiner* — Hannah Pak

(74) *Attorney, Agent, or Firm* — Tillman Wright, PLLC; David R. Higgins; Neal B. Wolgin

(57) ABSTRACT

High-melting antimicrobial polymer fibers and antimicrobial fabrics comprising such fibers are prepared by preparing a masterbatch of polymer pellets (e.g., PET), silver and copper salts, and a compounding agent which provides free flowing polymer pellets which can be prepared in advance, with a long shelf life. Polymer masterbatches prepared by the methods of the invention can produce limited color or off-white antimicrobial fibers and fabrics using conventional melt spinning manufacturing methods. Fabrics incorporating fibers of the present invention are potent inhibitors of Athlete's foot fungi, gram negative and gram positive bacteria, and drug resistant pathogens.

19 Claims, 14 Drawing Sheets

(56) References Cited

U.S. PATENT DOCUMENTS

| | | |
|---|---|---|
| 2009/0312456 A1 | 12/2009 | Changping |
| 2010/0124861 A1 | 5/2010 | Wendler et al. |
| 2010/0136073 A1 | 6/2010 | Preuss et al. |
| 2010/0267885 A1 | 10/2010 | Harimoto |
| 2011/0142900 A1 | 6/2011 | Ohta et al. |
| 2012/0083750 A1 | 4/2012 | Sansoucy |
| 2012/0094120 A1 | 4/2012 | Foss et al. |
| 2012/0141723 A1 | 6/2012 | Chuah et al. |
| 2012/0164449 A1 | 6/2012 | Foss |
| 2012/0222826 A1 | 9/2012 | Foss et al. |
| 2013/0152737 A1* | 6/2013 | Chen .................. B22F 9/18 75/370 |
| 2013/0209386 A1 | 8/2013 | Cove et al. |
| 2014/0259721 A1 | 9/2014 | Durdag et al. |
| 2014/0374941 A1 | 12/2014 | Foss et al. |
| 2015/0147570 A1 | 5/2015 | Foss |
| 2015/0342990 A1 | 12/2015 | Baumann |
| 2017/0006860 A1 | 1/2017 | Foss et al. |
| 2017/0044691 A1 | 2/2017 | Foss |

FOREIGN PATENT DOCUMENTS

| | | |
|---|---|---|
| JP | 01-096244 A | 4/1989 |
| JP | 01-139805 A | 6/1989 |
| JP | H02-087004 U | 7/1990 |
| JP | 10-310935 A | 11/1998 |
| JP | 2001-011734 A | 1/2001 |
| JP | 2004-197242 A | 7/2004 |
| JP | 2009-108448 A | 5/2009 |
| KR | 10-0766418 B1 | 10/2007 |
| WO | 2000053413 A1 | 9/2000 |
| WO | 2007078076 A1 | 7/2007 |
| WO | 2008010199 A2 | 1/2008 |
| WO | 2010024423 A1 | 3/2010 |
| WO | 2012088507 A2 | 6/2012 |
| WO | 2012088507 A3 | 6/2012 |
| WO | 2015023644 A2 | 2/2015 |
| WO | 2015184347 A1 | 12/2015 |

OTHER PUBLICATIONS

"International Search Report" and "Written Opinion" of PCT Application No. PCT/US2011/067184, dated Aug. 24, 2012 (9 pages).

Sigma-Aldrich, MSDS for Copper (II) phthalocyanine, reprinted Feb. 7, 2013 (6 pages).

* cited by examiner

Figure 1. Particle Size Distribution for Silver Sulfate Used in Examples Using Horiba LA-920 Instrument
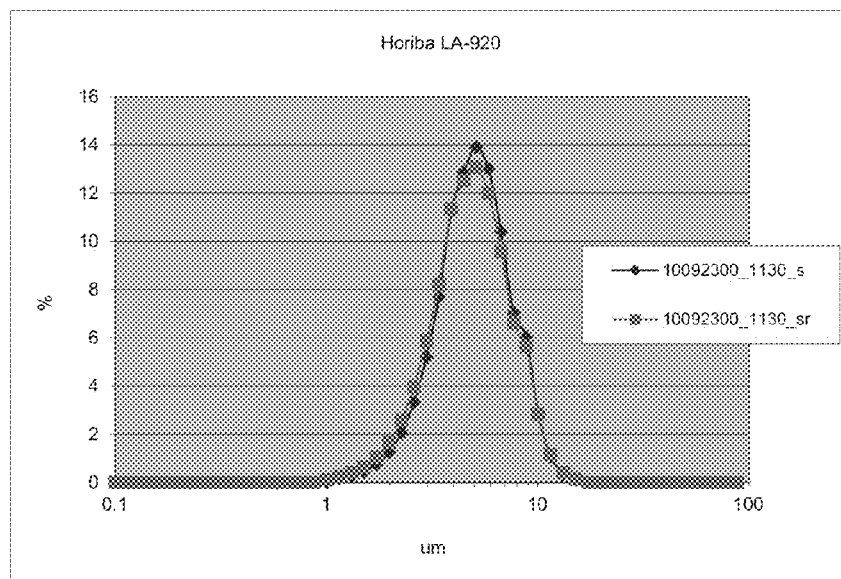

Figure 2a. DSC of Drawn and Heat set Polymer of Formula I (Example 15)
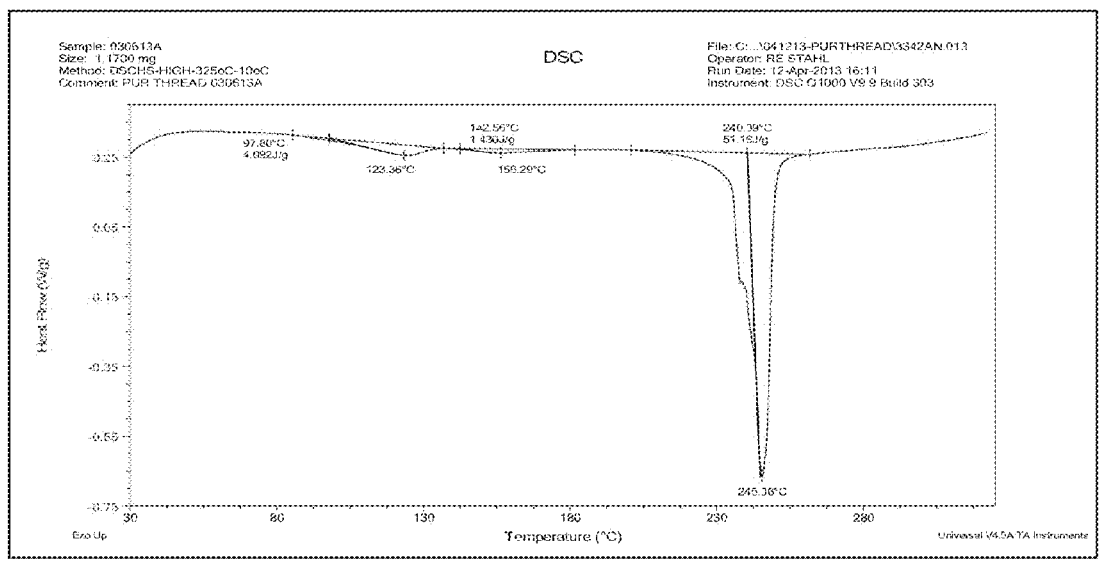

Figure 2b. DSC of Drawn and Heat set PET Polymer with only TiO$_2$ and Optical Brightener.
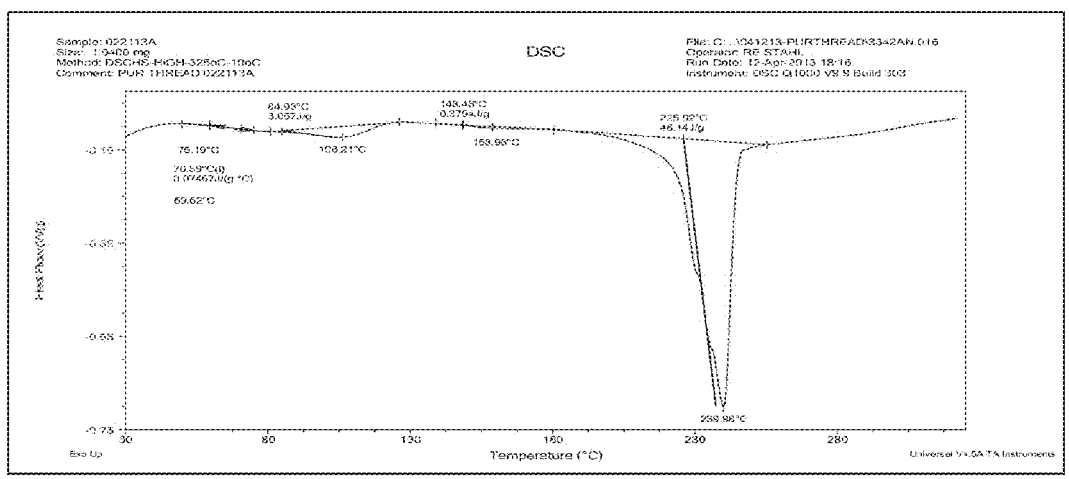

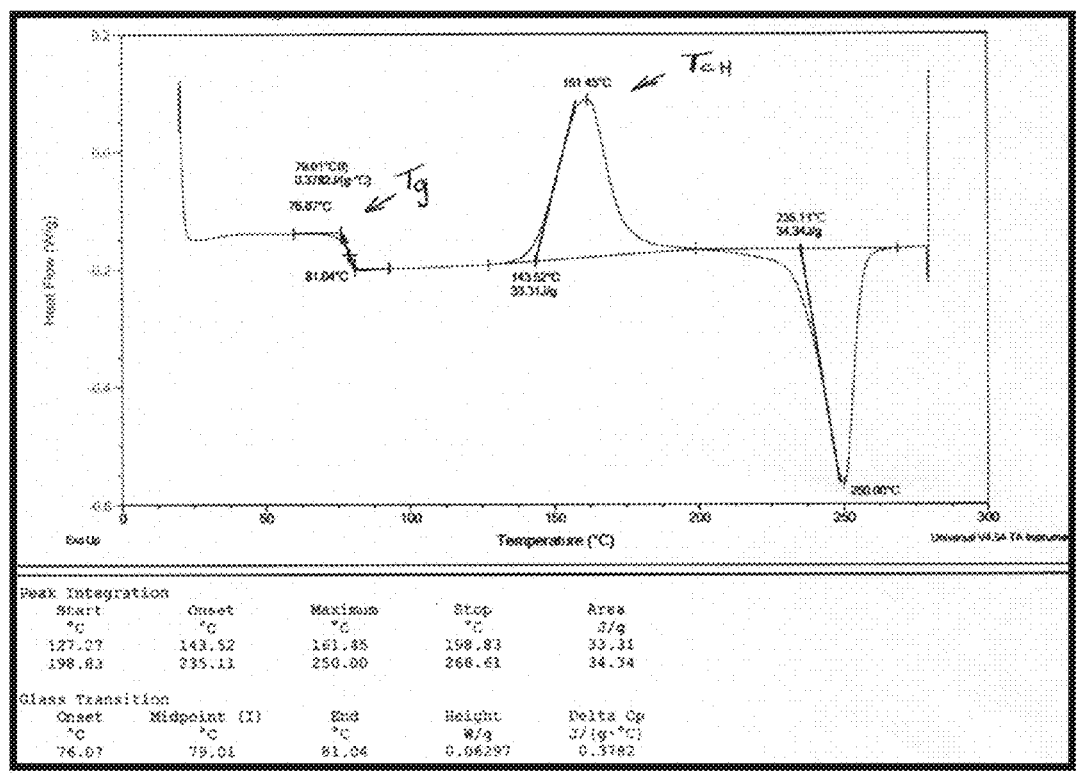
Figure 2c. DSC of Amorphous PET Polymer

Figure 3. SEM Image (left) Backscatter SEM Image (right) for Fiber of Example 14.
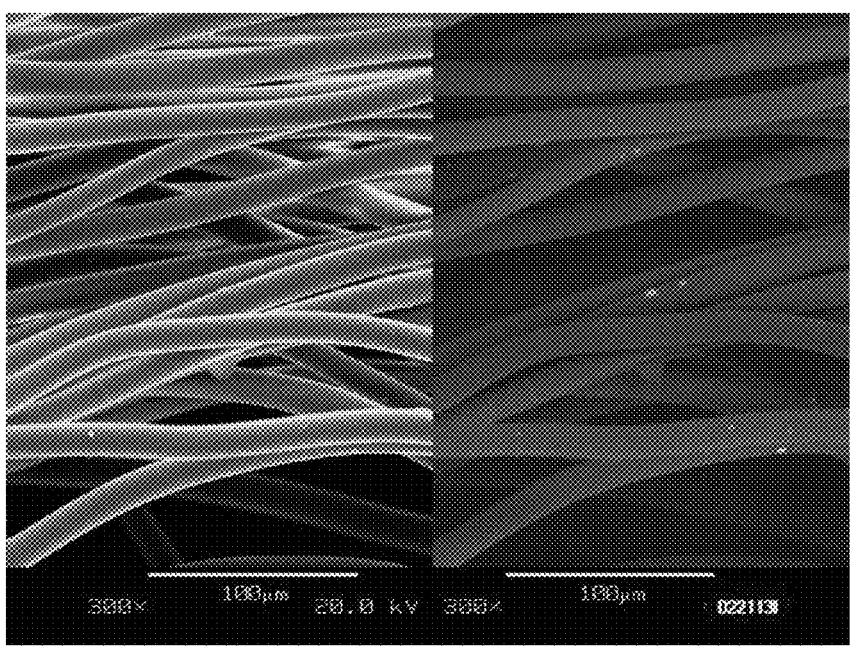

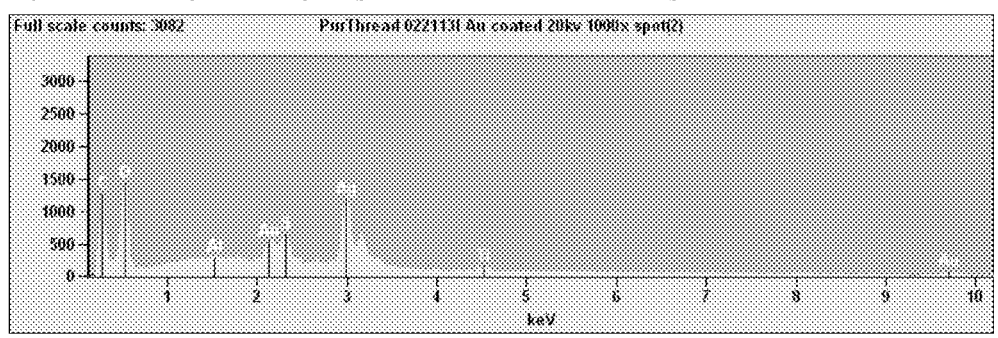
Figure 4. EDX Spectrum Spot Spectrum of Fiber from Example 14
| Element Line | Weight % | Weight % Error | Atom % | Atom % Error |
|---|---|---|---|---|
| C K | 34.9 | +/- 0.4 | 49.1 | +/- 0.6 |
| O K | 44.0 | +/- 0.7 | 46.4 | +/- 0.7 |
| Al K | 0.1 | +/- 0.1 | 0.1 | +/- 0.0 |
| S K | 2.7 | +/- 0.1 | 1.4 | +/- 0.0 |
| S L | --- | --- | --- | --- |
| Ti K | 0.9 | +/- 0.1 | 0.3 | +/- 0.0 |
| Ti L | --- | --- | --- | --- |
| Ag L | 17.4 | +/- 0.4 | 2.7 | +/- 0.1 |
| Ag M | --- | --- | --- | --- |
| Au L | --- | --- | --- | --- |
| Au M | --- | --- | --- | --- |
| Total | 100.0 | | 100.0 | |

Figure 5. Scanning Electron Microscope Image of Fibers
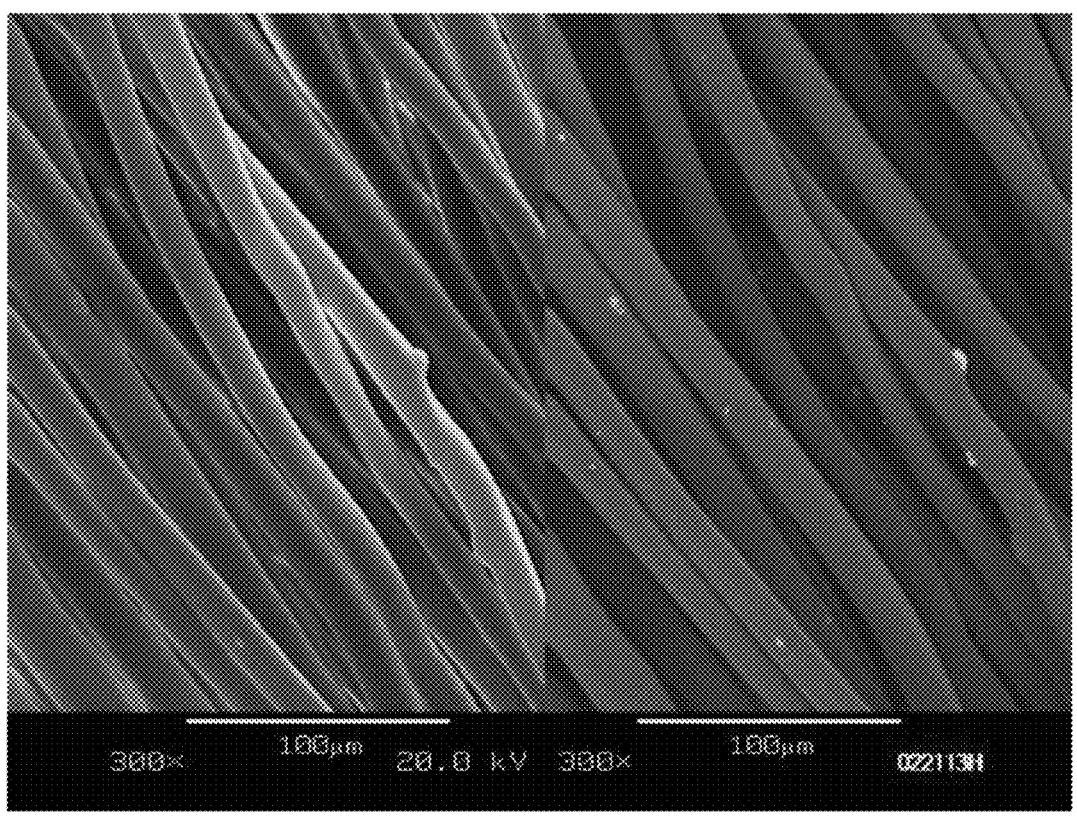

Figure 6. Scanning Electron Microscope Backscatter Image of Cut Polyester Fiber
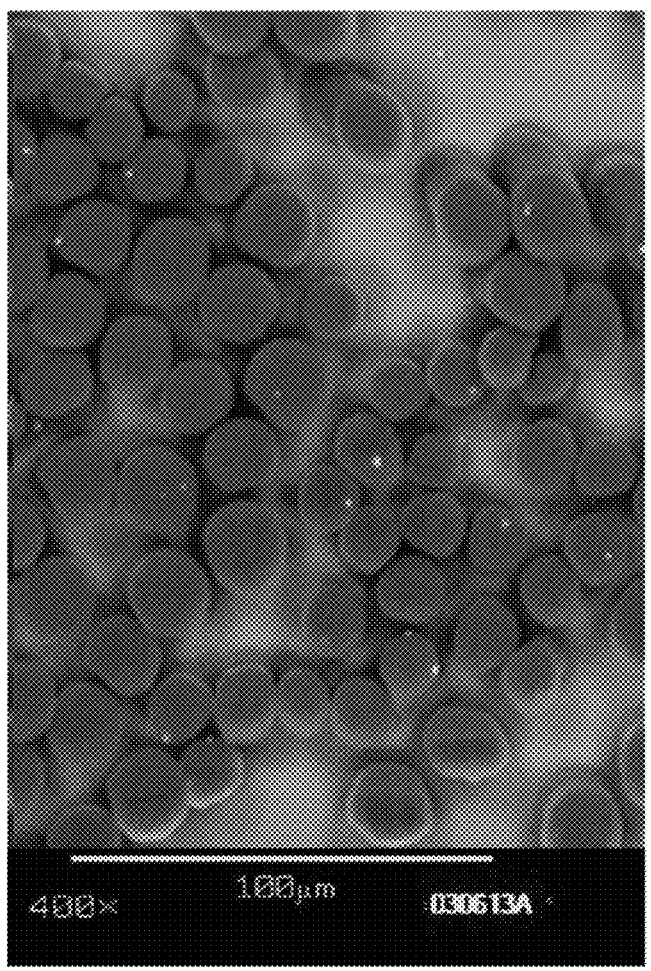

Figure 7. Energy Dispersive X-ray Analysis of SEM Cut Fiber Image
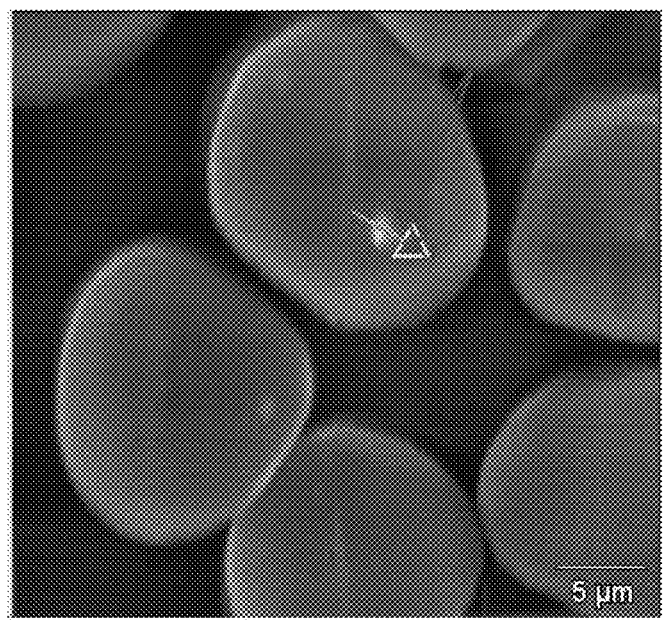

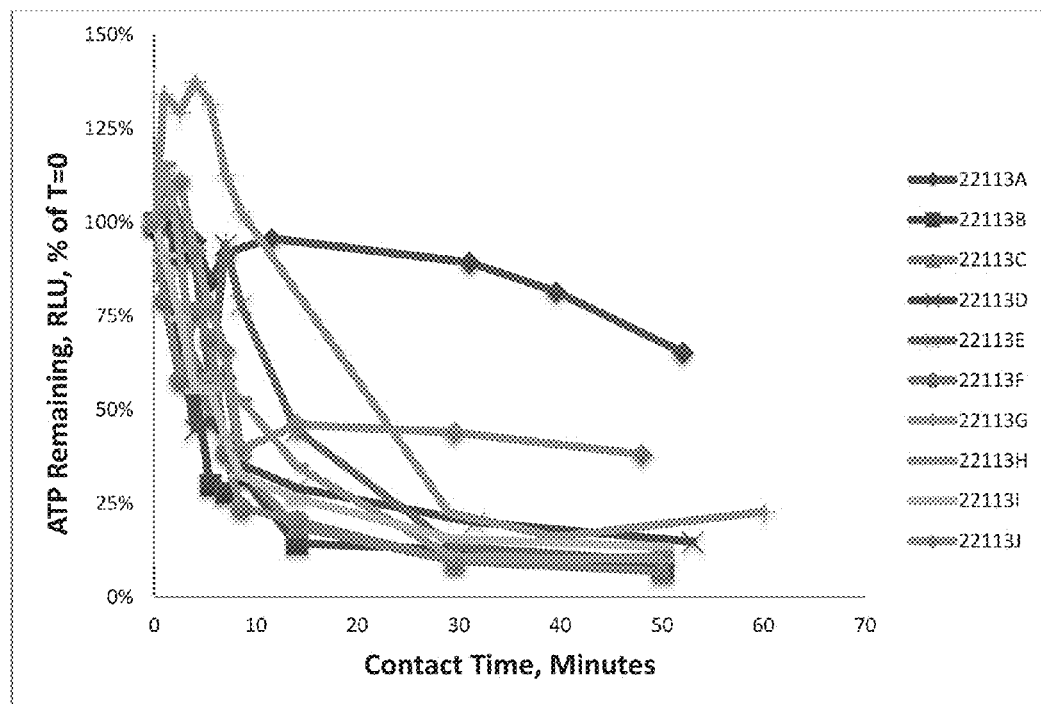
Figure 8. Rapid Test of *E. coli* Antibacterial Activity of Different Fiber Compositions

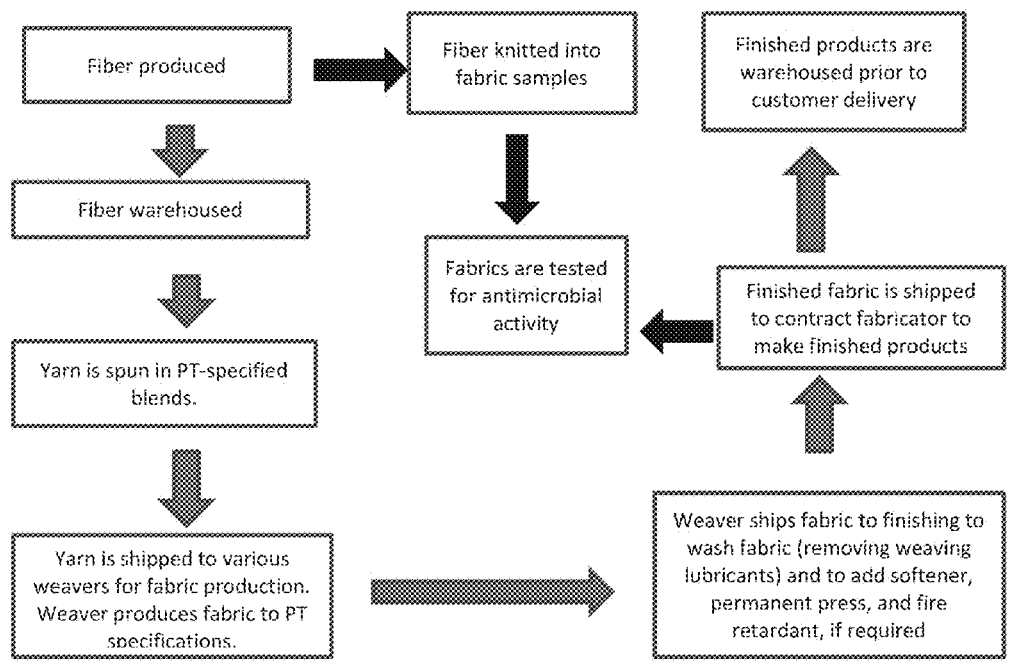
Figure 9. Flow Diagram of Method for Converting Fiber to Fabric

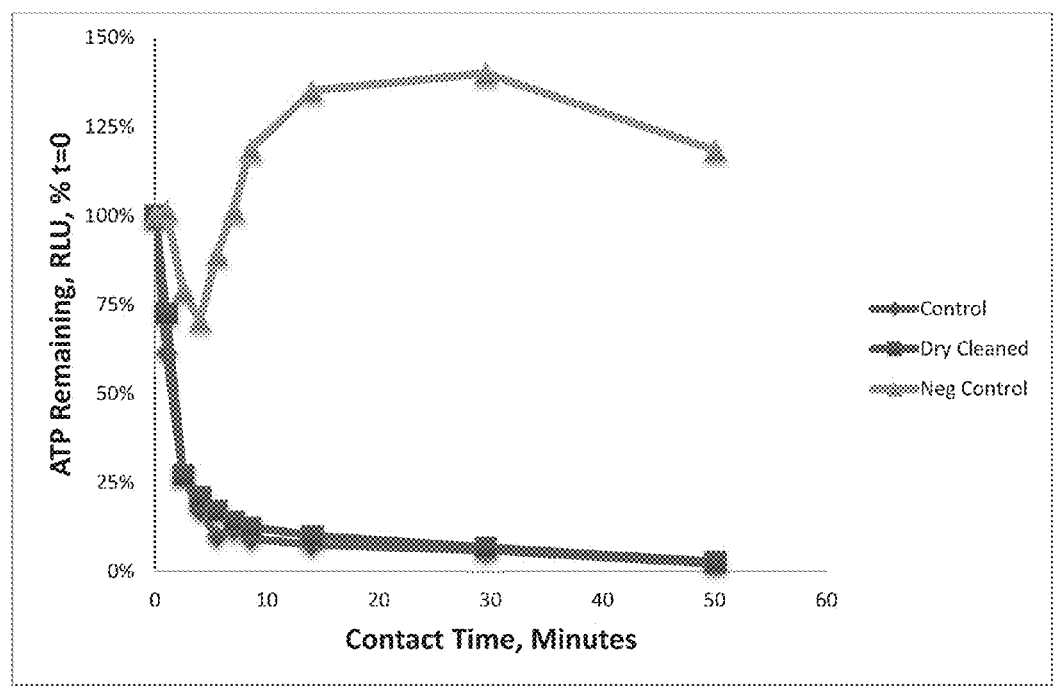
Figure 10. Effect of Dry Cleaning on Privacy Curtains

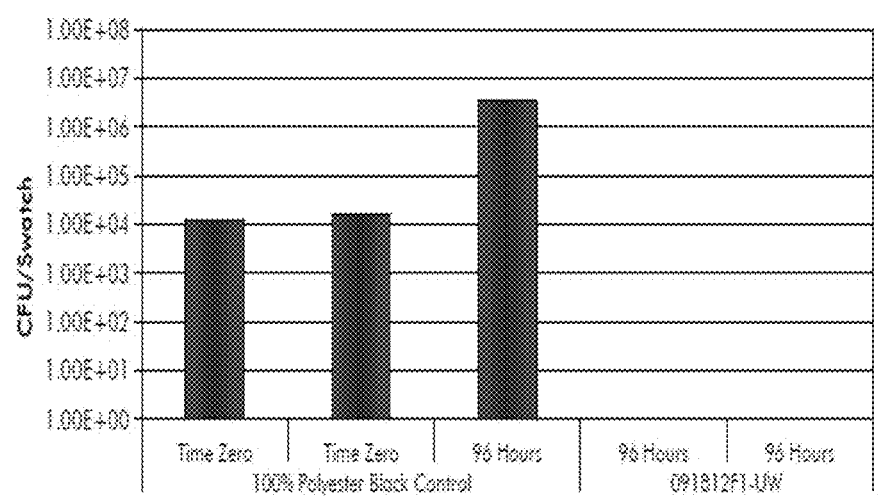
Figure 11. Antimicrobial Activity Against *T. mentagrophytes*

Figure 12. Images of Control and 0918121F1-UW Fabrics After Exposure to *T. menta*
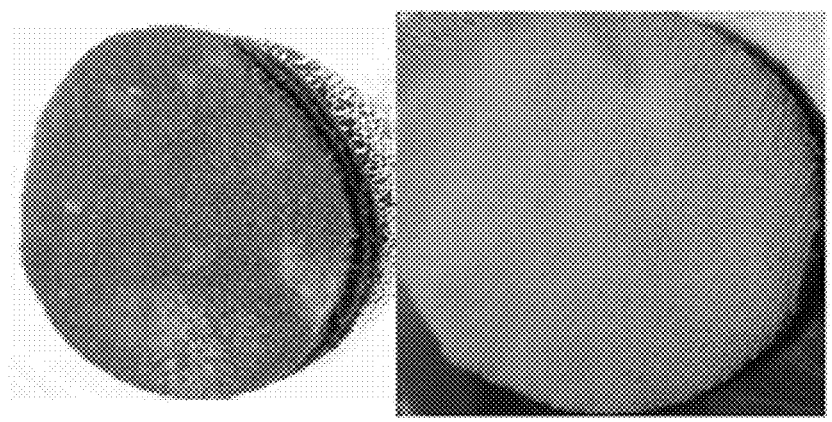

ANTIMICROBIAL AND ANTIFUNGAL POLYMER FIBERS, FABRICS, AND METHODS OF MANUFACTURE THEREOF

CROSS-REFERENCE TO RELATED APPLICATIONS

This application claims the benefit of U.S. Provisional Application No. 61/864,957, filed Aug. 12, 2013.

FIELD OF THE INVENTION

The present invention relates, inter alia, to the composition and production of antifungal and antibacterial polyester materials, for example fibers and fabric blends containing such fibers.

BACKGROUND OF THE INVENTION

Increasing attention has been paid to the dangers of microorganism contamination from everyday exposures. While primarily a concern for a wide range of healthcare facilities, and food processing and preparation facilities, it is also a concern for schools, public transport, the home and businesses. Healthcare facilities where microbial bio-burden is a concern include large multi-unit hospitals, specialized clinics, veteran affairs hospitals, long term care facilities, retirement homes and individual or group doctors or dental offices among others.

Drug resistant strains of pathogenic bacteria are being identified around the world, and the spread of these microorganisms from local to regional to worldwide is well documented. New microorganisms, or more virulent forms of existing micro-organisms, especially antibiotic resistant strains, are also being discovered, and can readily spread worldwide due to the growing ease of travel, and the developing worldwide market for goods. Microorganisms of concern include but are not limited to bacteria of all sorts, fungi, parasites, and many types of viruses. Although regular cleaning and good sanitation practices can be effective means of reducing microbial bio-burden, it would be beneficial to provide materials which are inherently resistant to, or minimize the spread of microorganisms.

The antimicrobial properties of silver have been known for a very long time. The pharmacological properties of silver are described in "Heavy Metals" by S. C. Harvey and in "Antiseptics and Disinfectants: Fungicides; Ectoparasiticides" by S. Harvey in The Pharmacological Basis of Therapeutics, Fifth Edition, Goodman and Gilman (editors), MacMillan Publishing Company, NY, 1975. The mechanism of action of silver has also been described by Clement and Jarrett in *Metabolism Based Drugs* 1(5-6), 467-482. Some basic mechanisms of action which have been identified include degradation of bacterial enzymes, cell wall degradation, inhibition of cell mitotic activity, degradation of cytoplasmic structures, and interaction with DNA bases. It is recognized in the literature that both metallic silver and silver ions are antimicrobial, but that ultimately antimicrobial activity is mediated through the dissolution of silver ions into the bacterial microenvironment.

Silver sulfate is a well-known, commercially available material that can be synthesized by conventional aqueous precipitation methods. The reaction of aqueous solutions of silver nitrate and sulfuric acid to form silver sulfate was described by Richards and Jones in *Z. anorg. Allg. Chem* 55, 72, (1907), and an improvement on the method was published by Hahn and Gilbert *Z. anorg. Allg. Chem* 258, 91, (1949). Silver salts are generally known to be thermally and photochemically unstable, forming brown, gray or black products. Silver sulfate may be reduced to its metallic state, with the corresponding oxidation of chemical elements in its environment. It can also be converted to or converted to silver oxide (black) or silver sulfide (black) by exposure to air. Silver metal generated by thermal reduction on a polymeric substrate will exhibit a UV absorption band at 390 nm which is attributable to the surface plasmon resonance of silver.

One use of silver based antimicrobials is for textiles. Various methods are known in the art to introduce antimicrobial properties to a target fiber. The approach of embedding inorganic antimicrobial agents, such as zeolites, into low melting components of a conjugated fiber is described in U.S. Pat. Nos. 4,525,410, and 5,064,599. In another approach, the antimicrobial agent can be delivered during the process of making a synthetic fiber such as those described in U.S. Pat. Nos. 5,180,402, 5,880,044, and 5,888,526, or via a melt extrusion process as described in U.S. Pat. Nos. 6,479,144 and 6,585,843. In yet another process, an antimicrobial metal ion can be ion-exchanged with an ion-exchange fiber as described in U.S. Pat. No. 5,496,860. High-pressure laminates containing antimicrobial inorganic metal compounds are disclosed in U.S. Pat. No. 6,248,342. Deposition of antimicrobial metals or metal-containing compounds onto a resin film or fiber has also been described in U.S. Pat. Nos. 6,274,519 and 6,436,420. An antimicrobial mixture of zinc oxide and silver sulfate on an inorganic powder support is disclosed in JP 08133918. An antimicrobial masterbatch formulation is disclosed in JP 2841115B2 wherein a silver salt and an organic antifungal agent are combined in a low melting wax to form a masterbatch with improved mixing and handling safety. More specifically, silver sulfate was sieved through a 100 mesh screen (particles sizes less than about 149 microns), combined with 2-(4-thiazolyl)benzimidazole and kneaded into polyethylene wax. This masterbatch material was then compounded into polypropylene, which was subsequently injection molded into thin test blocks which exhibited antibacterial properties with respect to *E. coli* and *Staphylococcus*, and antifungal properties with respect to *Aspergillus niger*. Similar masterbatches are also described in JP 03271208, wherein a resin discoloration-preventing agent (e.g. UV light absorbent, UV light stabilizer, antioxidant) is also incorporated.

Silver sulfate has been used as an antimicrobial agent in multiple medical applications. Incorporation of inorganic silver compounds in bone cement to reduce the risk of post-operative infection following the insertion of endoprosthetic orthopaedic implants was proposed and studied by J. A. Spadaro et al (Clinical Orthopaedics and Related Research, 143, 266-270, 1979). Silver chloride, silver oxide, silver sulphate and silver phosphate were incorporated in polymethylmethacrylate bone cement at 0.5% concentration and shown to significantly inhibit the bacterial growth of *Staphylococcus aureus, Escherichia coli* and *Pseudomonas aeruginosa*. Antimicrobial wound dressings are disclosed in U.S. Pat. No. 4,728,323; wherein a substrate is coated with an antimicrobially effective film of a silver salt, preferably silver chloride or silver sulfate. Antimicrobial wound dressings are disclosed in WO2006113052A2, wherein aqueous silver sulfate solutions are dried onto a substrate under controlled conditions to an initial color, which is color stable for preferably one week under ambient light and humidity conditions. An antimicrobial fitting for a catheter is disclosed in U.S. Pat. No. 5,049,140 which describes a tubular member composed of a silicone/polyurethane elastomer in which is uniformly dispersed about 1 to 15% wt. of an antimicrobial agent, preferably silver sulfate. A moldable plastic composite comprising cellulose and a urea/formaldehyde resin is disclosed in WO 2005/080488A1, wherein a silver salt, specifically silver sulfate, is incorporated to provide a surface having antiviral activity.

Despite various references to the proposed use of silver salts as antimicrobial agents in various polymers as referenced above, there is little or no disclosure in the art of methods for preparing silver-containing materials comprising higher melting polymers such as polyethylene terephthalate (PET) polyester. Even the relatively thermally stable silver sulfate salt is converted to metallic silver when heated excessively in an organic matrix at the temperatures necessary to melt and extrude PET, for example in processes for making polyester (e.g., PET) fiber. Other silver salts such as the silver halides and silver nitrate are even more thermally sensitive than silver sulfate and are thus more prone to reduction to metallic silver if processed at high temperature, for example under typical polyester fiber production process conditions.

In order to avoid problems with the thermal instability of silver salts during fiber production, various processes have been proposed in which different dispersions of silver salts in multi-component mixtures have been applied to fabrics of different compositions as topical agents after the fiber has been extruded, or after the fabric has been constructed. However, fabrics in which e.g. silver salts have been topically applied exhibit poor laundering properties and leaching of the topical silver salt from the topical fabric coating. It is also difficult to control the amount of silver salt topically absorbed onto the surface of the fiber or the fabric because of the various finishing solutions, dyes flame retardants or other agents commonly applied to fibers or textiles. Topical coatings on textile grade fibers or fabrics may have utility in certain settings, but are viewed as a fundamentally different technology relative to a textile grade polyester fiber having the antimicrobial agent incorporated into the fiber during the fiber extrusion process.

In addition, the use of metallic silver nanoparticles as antimicrobial and antifungal agents in textiles has been attempted but has generally been unsuccessful due to problems with clumping and other challenges, and it is been difficult to obtain a controlled, uniform dispersion and concentration of the metallic silver nanoparticles in the final textile product. Theoretically, the high surface area of the metallic silver nanoparticles offers an advantage over micron sized metallic silver particles as antimicrobial and/or antifungal agents due to the nature of the ion release mechanism. The release mechanism involves water or oxygen mediated oxidation and dissolution of silver ions from the silver metal surface, which occurs in proportion to the surface area. However, metallic silver nanoparticles are difficult to incorporate into textiles to produce a product having desirable properties including durable antibacterial and/or antifungal biocidal activity after repeated use and washings.

A method for incorporating metallic silver nanoparticles into polyester and other synthetic polymeric fibers is disclosed in U.S. Pat. No. 8,183,167. However, this technology suffers from the disadvantage that metallic silver nanoparticles release silver ions more slowly than particles of silver salts such as silver sulfate. In addition, it is recognized in the literature that metallic silver nanoparticles can be absorbed into cells directly and have their own toxicity characteristics separate from that of silver ions. Incorporation of metallic silver nanoparticles into the fiber during polymer extrusion, or topically treating fibers or fabrics with metallic silver nanoparticles after extrusion, is considered a very different technology compared to incorporating silver salt particles into the extruded fiber.

Foss et al. in U.S. Pat. Nos. 6,723,428, 6,841,244, and 6,946,196 disclosed multilayer and multicomponent antimicrobial fabrics and articles employing preferably silver-containing zeolites as antimicrobial agents, for example in a thin "shell" layer on the exterior of the fiber, in a relatively low melting carrier polymer (e.g. PETG), or in a latex which is used as a vehicle for impregnating e.g. a shoe insole. When a low melting polymer carrier is used, the fabric containing the low melting polymer and incorporated antimicrobial agent is heat activated to melt the polymer and disperse the antimicrobial agent throughout the fabric.

BRIEF SUMMARY OF THE INVENTION

In one embodiment, the present invention is directed to a novel polyester fiber comprising a high melting polymer (e.g., a polymer melting in the range of about 260° C. or higher) which has a processing temperature of at least about 290° C. such as polyethylene teraphthalic acid polymer (PET), nylon 6,6, or other high-melting fibers described herein, a silver salt of formula $Ag_aX_bY_cZ_d$ such as a silver sulfonate or silver I sulfate, with a particle size of between 800 nanometers and 20 micrometers, a copper salt of formula $Cu_aX_bY_cZ_d$, such as copper II sulfate, and a compounding agent. A nonlimiting list of suitable compounding agents include one or more of: polydimethylsiloxane (CAS 63148-62-9), dimethylsiloxane, hydroxyl terminated polydimethylsiloxane (CAS 70131-67-8), amorphous silica (CAS 7631-86-9), aliphatic petroleum distillates (CAS 64742-47-8), or liquefied petroleum gas (CAS68476-86-8). The novel composition also may include additional ingredients, such as pigments (e.g. titanium dioxide), and optical brighteners such as the commercially available OB1 (4,4'-bis(benzoxazol-2-yl) stilbene). In various embodiments, the silver salt is dispersed in the fiber (e.g. polyester or PET fiber) at a concentration of about 0.05% to about 1.0% by weight. The silver salt $Ag_aX_bY_cZ_d$ may have an oxidizing agent such as $NaIO_4$ incorporated in it at a concentration of about 0.2 to about 5% weight of the $Ag_aX_bY_cZ_d$. In various embodiments the copper salt is dispersed in the polyester fiber at a concentration of about 0.01% to about 1.0% by weight. In various embodiments the compounding agent is present in the final polyester at a concentration of about 0.01% to about 0.1% by weight. The titanium dioxide is present in the final polyester at a concentration of about 0.03% to about 0.6% by weight. The optical brightener (e.g., OB1) may be present in the final polyester at a concentration of about 0.01% to about 0.1% by weight. Thus, in some embodiments, the final polyester could be described by a Formula I: $Ag_aX_bY_cZ_d$ (about 0.05 to about 0.50%)+$Cu_aX_bY_cZ_d$ (about 0.01 to about 0.1%)+$NaIO_4$ (about 0.0002 to about 0.025%)+compounding agent (about 0.01 to about 0.1%)+$TiO_2$ (about 0.03 to about 0.6%)+OB1 (about 0.01 to about 0.1%)+PET (about 99.85% to about 98.5%). Wherein:

PET is a polyethylene terephthalate polymer
OB 1 is an commercial optical brightener
$NaIO_4$ is sodium periodate
$TiO_2$ is titanium dioxide
Ag is silver I or silver II and a is 1 to 4
$X_b$ is sulfur (S) and b is 1 to 4
$Y_c$ is oxygen (O) and c is 2 to 8

$Z_d$ is defined as an alkyl group R, or an aryl group Ar and d is 0 or 1

Wherein
R is
hydrogen,
$C_1$-$C_{14}$ alkyl
$C_3$-$C_8$ cycloalkyl
$C_1$-$C_8$ alkyl optionally substituted by $C_3$-$C_6$ cycloalkyl,
$C_1$-$C_8$ alkyl optionally substituted by $C_6$-$C_{10}$ aryl
and Ar is $C_6$-$C_{10}$ aryl optimally substituted by R, halogen (F, Cl, Br, I)

In another embodiment, the present invention is directed to methods of manufacturing antimicrobial fiber compositions as described herein, wherein the silver salt is exposed to a minimal heat history. Such methods incorporate a master batch approach, in which the master batch has between about a 4% and about 20% loading of the silver salt of formula $Ag_aX_bY_cZ_d$.

The silver salt is adhered to the surface of the high melting polymer (e.g. PET) pellet in a uniform manner such that about 10 to about 90% of the surface of individual pellets, using a mixture of the compounding agents listed herein, is coated. Polymer pellets such as PET are either round, cubic, or cylindrical, and have either smooth surfaces or irregular surfaces. This "compounded master batch" can be described by the following formula: [$Ag_aX_bY_cZ_d$ ($w_1$%)/$Cu_aX_bY_cZ_d$ ($wt_2$%)/Compounding Agent ($wt_3$%)/PET($wt_4$%)], wherein the sum of the weight percents is 100%, and the weight percent of the $Ag_aX_bY_cZ_d$ is about 1% to about 26% and the weight percent of the $Cu_aX_bY_cZ_d$ is about 0.1% to about 2.6% and the weight % of the compounding agent is about 0.15 to about 3%, and the polymer (e.g. PET) makes up the difference. The compounded master batch is prepared by combining freshly dried polymer (e.g. PET) with the compounding agent and mixing thoroughly such that the compounding agent evenly covers the surface of the polyester pellets, e.g., by tumbling the pellets in the presence of the compounding agent. Once the pellets are covered, a mixture of the appropriate amount of $Ag_aX_bY_cZ_d$ powder and $Cu_aX_bY_cZ_d$ powder are mixed together and then added to the polymer pellets covered with the compounding agent, and mixed until a free flowing mass of coated polymer pellets is obtained. The modified polymer pellets prepared in the described manner, are subsequently mixed with master batches of titanium dioxide, OB1 and unmodified polymer at ambient temperature and humidity, prior to being loaded into an extruder which, in the case of PET, is heated at about 295° C.

In another embodiment, the process of the present invention is capable of producing fiber having an off-white color. Such off-white fibers can be used to produce fabrics which can be described as having "limited" color, in other words, white or off-white.

The fibers and the fabrics of the present invention, as described herein, are surprisingly able to kill microbes deposited on their surfaces. In specific embodiments, the fibers and fabrics of the present invention are surprisingly active against gram negative bacteria or gram positive bacteria. In still other embodiments, the fibers and fabrics of the present invention are surprisingly able to kill microbes deposited on the surface of the fiber or resulting fabric, including microbes known to be resistant to conventional antimicrobial agents, including carbapenemase producing *Klebsiella pneumonia*, Methicillin Resistant *Staphylococcus aureus*, Vancomycin Resistant *Enterococcus*, MDR *Pseudomonas aeruginosa*, MDR *Acinetobacter*, $3^{rd}$ Generation Cephalosporin Resistant *E. cloacae*, *Acinetobacter baumannii*, and Fluconazole Resistant *Candida albicans*.

The fibers and the fabrics of the present invention, as described herein, are also surprisingly active against fungal microbes of different types, in particular against fungi associated with Athlete's foot, for example the fungus *Trichophyton mentagrophytes* (*T. menta*) which is an important component of the fungi that make up Athlete's foot infections.

In still other embodiments, the fibers and fabrics of the present invention can be washed 25 to 100 times using standardized washing procedures such as the AATCC 61 protocol, and maintain their antibacterial and antifungal activity, for example as described herein.

BRIEF DESCRIPTION OF THE DRAWINGS

Further features, embodiments, and advantages of the present invention will become apparent from the following detailed description with reference to the drawings, wherein:

FIG. 1 is a graphical illustration of a typical particle size distribution of silver sulfate particles used in the present invention;

FIGS. 2a-2c are graphical illustrations of DSC characteristics of various samples;

FIG. 3 is a set of SEM data for fibers of Example 14, including the normal SEM image and the backscatter SEM image;

FIG. 4 is an EDX spot spectrum for fibers of Example 14;

FIG. 5 is an SEM image (left) and a backscatter detection SEM image (right) of a polyester fiber according to the present invention with antimicrobial silver salt (silver sulfate) particles incorporated in the fibers;

FIG. 6 is an SEM backscatter image of cut polyester fibers according to the present invention;

FIG. 7 is an EDX analysis of an SEM image of cut polyester fibers according to the present invention;

FIG. 8 is a graphical illustration of the antibacterial properties of the fiber compositions of Table 2 against *E. coli*;

FIG. 9 is a flow diagram of an exemplary method of converting fiber to fabric;

FIG. 10 is a graphical illustration of an effect of dry cleaning on fabric privacy curtains;

FIG. 11 is a bar graph illustrating the results set forth in Table 12 concerning antimicrobial activity against *T. mentagrophytes*; and FIG. 12 is a set of images comparing a control fabric (left) without antimicrobial silver particles and fabric 091812F1-UW (right) after exposure to *T. mentagrophytes*.

DETAILED DESCRIPTION OF THE INVENTION

All patent applications, patents, patent publications, and literature references (including ASTM or other analytical methods) cited in this specification, whether referenced as such, are hereby incorporated by reference in their entirety. In the case of inconsistencies, the present description, including definitions, is intended to control.

The present invention provides for fibers, filaments, yarns, fabric, textiles and the like possessing excellent long-term antimicrobial efficacy, even after a substantial number of washings. Such properties are realized by the use of fibers or filaments having incorporated therein, by the methods of the present invention as described herein, a particular silver salt and reagents used to incorporate the silver salt into the fibers or filaments.

As used herein and as context allows, the terms "textile" and "textiles" are intended to include fibers, filaments, yarns and fabrics, including knits, wovens, non-wovens, and the like. For purposes of this invention, textiles may be composed of or made from synthetic fibers or combinations of synthetic fibers and natural fibers. In various embodiments, textiles in the form of fibers and yarns may be of a size or denier ranging from about 1 denier per filament to about 3 denier per filament, more particularly from less than about 1 denier per filament to about 2 denier per filament. However, other fiber or yarn sizes may be employed.

It is also contemplated that the fibers or yarns of the present invention may be mono-component, multi-component or bi-component fibers or yarns, including those that may be splittable, or which may have been partially or fully split, along their length by chemical or mechanical action as well as those of the core-sheath type construction. The fibers or yarns may be multi- or mono-filament, may be false-twisted or twisted, or may incorporate multiple denier fibers or filaments into one single yarn through twisting, melting and the like. Fabrics may be formed of any of the foregoing fibers and yarns or combinations thereof. For example, a fabric may be wholly or partially made of multi- or bi-component fibers and yarns. Additionally, the fabrics may be made of fibers and yarns of different compositional make-up, including combinations of natural and synthetic fibers and yarns, combinations of natural fibers and yarns, or combinations of synthetic fibers and yarns. Fabrics may be comprised of fibers and yarns such as staple fibers, filament fiber, spun fiber, or combinations thereof. Furthermore, the textiles may be comprised of antimicrobial fibers and yarns in combination with fibers and yarns free of the antimicrobial agents.

As noted, textiles of the present invention may comprise only fibers according to the present invention, or may be composed of or made from a combination of natural or synthetic fibers with the antimicrobial synthetic fiber(s) of the present invention. A non-limiting list of natural fibers includes wool, cotton, flax, hemp, bamboo fibers, and blends thereof. Synthetic fibers include fibers made of, for example, polyesters, acrylics, polyamides, polyolefins, polyaramids, polyurethanes, regenerated cellulose (i.e., rayon) and blends thereof. More specifically, polyester fibers include, but are not limited to, polyethylene terephthalate, poly(trimethylene terephthalate), poly(triphenylene terephthalate), polybutylene terephthalate, aliphatic polyesters (such as polylactic acid (PLA), polyglutaric acid (PLG), and combinations thereof, and are generally characterized as long chain polymers having recurring ester groups. Polyamides include, but are not limited to, nylon 6; nylon 6,6; nylon 12; nylon 6,10, nylon 1,1 and the like and are characterized by long-chain polymers having recurring amide groups as an integral part of the polymer chain. Polyolefins include, but are not limited to polypropylene, polyethylene, polybutylene, polytetrafluoroethylene, and combinations thereof. Polyaramids include, but are not limited to, poly-p-phenyleneterephthalamid (i.e., Kevlar®), poly-m-phenyleneterephthalamid (i.e., Nomex®), and combinations thereof.

Any of the synthetic polymers disclosed herein, having a high melting point, e.g. above about 250° C., and as high as about 310° C. (or higher) are particularly suitable for use in the present invention, as it is particularly difficult to process such high melting point polymers, containing the antimicrobial silver and copper salts of the present invention, without thermally degrading in particular the silver salts. In addition, synthetic polymers suitable for use in the present invention include polymers which require elevated processing conditions, for example processing conditions above about 290° C. In order to melt process (e.g., melt spin) polymers suitable for forming fibers in textiles, the processing temperature must be sufficiently high, depending upon the additives (if any) present in the composition, and/or the molecular weight of the polymer, such that the melt viscosity is sufficiently low to form good quality fibers. Accordingly, polymers such as PET, which has a melting point of approximately 265° C., are often processed at temperatures ranging from about 290° C. to about 310° C. in order to achieve melt viscosities sufficiently low to form good quality fibers. Thus, polymers requiring melt processing at temperatures above about 290° C., for example about 290° C., about 295° C., about 300° C., about 305° C., about 310° C., about 315° C., or about 320° C., inclusive of all values, ranges or subranges there between, and irrespective of polymer melting point, are suitable for use in the present invention.

The compositions and methods of the present invention are not limited to high-melting polymers, but can also be applied to other polymers typically used to form fibers via a melt-spinning process. Because the process of the present invention reduces the thermal history experienced by a polymer, particularly in the preparation of a masterbatch containing antimicrobial agents such as silver salts, the present invention is particularly efficacious for preparing antimicrobial fibers of relatively high-melting point polymers such as PET. In some embodiments, the polyester compositions and fibers of the present invention can also include small amounts of polymeric additives, such as liquid crystal polymers (LCP), polyamides, (co-) polymers based on acrylics. Such additives, when present in small amount can improve the properties of the polyester (e.g. PET), for example by forming micro-fibrils in the polyester melt, which can, for example, increase the windup speed of the PET fibers. The compositions and methods of the present invention may also be suitable for use with lower melting polymers even those which may require lower processing temperatures, if the polymers and compositions are thermally sensitive at the temperature required to melt spin good quality fibers.

The textile substrate may be dyed or colored with any type of colorant, such as pigments, dyes, tints and the like, to provide other aesthetic features for the end user. Other additives may also be present on and/or within the textile substrate, including antistatic agents, brightening compounds, nucleating agents, antioxidants, UV stabilizers, fillers, permanent press finishes, softeners, lubricants, curing accelerators, and soil release agents, which improve the wettability and washability of the textile. All of such additional materials are well known to those skilled in the art and are commercially available.

In accordance with one embodiment, the present invention is directed towards a novel composition of high melting polymer fibers (e.g. having a melting point of greater than about 260° C.) for example polyester fibers comprising a conventional polyethylene terephthalic acid polymer (PET). However, the compositions and process of the present invention can also be used to prepare superior antimicrobial compositions of lower melting polymers such as PLA, nylon 6, nylon 6,6, and polypropylene. The compositions of the present invention further comprise a silver salt $Ag_aX_bY_cZ_d$ such as silver sulfate with a particle size of between about 800 nanometers and about 20 micrometers, and in particular with particles having a size distribution ranging from about 1 to about 10 microns with a median of about 5 microns, a copper salt of formula $Cu_aX_bY_cZ_d$, such as copper II sulfate pentahydrate or anhydrous copper II sulfate, and in particular anhydrous copper II sulfate, and a compounding agent comprising one or more of the following materials: polydimethylsiloxane (CAS 63148-62-9), hydroxyl terminated polydimethylsiloxane (CAS 70131-67-8), amorphous silica (CAS 7631-86-9), aliphatic petroleum distillates (CAS 64742-47-8), or liquefied petroleum gas (CAS68476-86-8). The composition may optionally include pigments such as titanium dioxide, and a commercially available optical brightener such as OB1 (4,4'-bis(benzoxazol-2-yl) stilbene) from Dalton Clariant. Other optional components include pigments such as Phthallo Blue, Carbon Black, quinacridone violet, etc., including any pigments dyes, coloring agents, or brightening agents conventionally used in textile manufacturing.

The silver salt, which can be any of the silver salts $Ag_aX_bY_cZ_d$ discussed herein, particularly silver sulfate, is incorporated into the fiber, and typically dispersed in the fiber at a concentration of up to about 1% by weight, such from about 0.05% up to about 1% by weight, or from about 0.05% to about 0.50% by weight, including about 0.05, about 0.06, about 0.07, about 0.08, about 0.09, about 0.1, about 0.15, about 0.2, about 0.25, about 0.3, about 0.35, about 0.4, about 0.45, about 0.5, about 0.55, about 0.6, about 0.65, about 0.7, about 0.75, about 0.8, about 0.85, about 0.9, about 0.95, and about 1% by weight, inclusive of all ranges and subranges therebetween. The silver salt $Ag_aX_bY_cZ_d$ may have an oxidizing agent such as $NaIO_4$ incorporated in it at a concentration of about 0.2 to about 5% weight of the $Ag_aX_bY_cZ_d$, including concentrations of about 0.2, about 0.25, about 0.3, about 0.35, about 0.4, about 0.45 m about 0.5, about 0.55, about 0.6, about 0.65, about 0.7, about 0.75, about 0.8, about 0.85, about 0.9, about 0.95, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, about 3.0, about 3.1, about 3.2, about 3.3, about 3.4, about 3.5, about 3.6, about 3.7, about 3.8, about 3.9, about 4.0, about 4.1, about 4.2, about 4.3, about 4.4, about 4.5, about 4.6, about 4.7, about 4.8, about 4.9, and about 5.0% by weight, and all ranges and subranges therebetween. The copper salt is dispersed in the fiber at a concentration of about 0.01% to about 1.0%, such as about 0.01% to about 0.5% by weight, including about 0.01, about 0.02, about 0.03, about 0.04, about 0.05, about 0.06, about 0.07, about 0.08, about 0.09, about 0.1, about 0.2, about 0.25, about 0.3, about 0.35, about 0.4, about 0.45, about 0.5, about 0.55, about 0.6, about 0.65, about 0.7, about 0.75, about 0.8, about 0.85, about 0.9, about 0.95, or about 1.0% by weight, inclusive of all ranges and subranges therebetween. The compounding agent is present in the final polymer composition (e.g. the fiber) at a concentration of about 0.01% to about 0.1% by weight, including about 0.01, about 0.02, about 0.03, about 0.04, about 0.05, about 0.06, about 0.07, about 0.08, about 0.09, and about 0.1% by weight, inclusive of all ranges and subranges therebetween. The amount of compounding agent, as described herein, is limited to the range of about 0.01 wt. % to about 0.1 wt. % so that the physical properties of the polymer component (e.g. PET) and the antimicrobial additives remains unaffected. In addition, these levels of compounding agent facilitate migration of the antimicrobial particles to the surface of the fibers where they can provide excellent activity against a wide range of bacteria and fungi, rather than allowing them to be trapped in the center of the fibers which reduces the antimicrobial activity. The titanium dioxide, if added to the final polymer composition, is present at a concentration of about 0.03% to about 0.6% by weight, including about 0.03, about 0.04, about 0.05, and about 0.06% by weight, inclusive of all ranges and subranges therebetween. The optical brightener (e.g., OB1) if added, may be present in the final polymer composition at a concentration of about 0.01% to about 0.1% by weight, including about 0.01, about 0.02, about 0.03, about 0.04, about 0.05, about 0.06, about 0.07, about 0.08, about 0.09, and about 0.1% by weight, inclusive of all ranges and subranges therebetween. Thus, the final polyester could be described in one embodiment by a Formula I: $Ag_aX_bY_cZ_d$ (about 0.05 to about 0.50%)+$Cu_aX_bY_cZ_d$ (about 0.01 to about 0.1%)+$NaIO_4$ (about 0.0002 to about 0.025%)+Compounding agent (about 0.01 to about 0.1%)+$TiO_2$ (about 0.03 to about 0.6%)+OB1 (about 0.01 to about 0.1%)+PET (about 99.85% to about 98.5%).

wherein

PET is a polyethylene terephthalate polymer

OB1 is a commercial optical brightener $NaIO_4$ is sodium periodate $TiO_2$ is titanium dioxide Ag is silver I or silver II and a is 1 to 4

$X_b$ is sulfur (S) and b is 1 to 4

$Y_c$ is oxygen (O) and c is 2 to 8

$Z_d$ is defined as an alkyl group R, or an aryl group Ar and d is 0 or 1

Wherein

R is hydrogen, $C_1$-$C_{14}$ alkyl $C_3$-$C_8$ cycloalkyl $C_1$-$C_8$ alkyl optionally substituted by $C_3$-$C_6$ cycloalkyl, $C_1$-$C_8$ alkyl optionally substituted by $C_6$-$C_{10}$ aryl And Ar is $C_6$-$C_{10}$ aryl optimally substituted by R, halogen (F, Cl, Br, I)

In another embodiment, the present invention is directed to methods of manufacturing an antimicrobial (e.g., polyester) fiber as described herein, wherein the silver salt is exposed to a minimal heat history. Typical melt processing conditions for preparing textile fibers includes forming a masterbatch (e.g. including antimicrobial agents, pigments, etc.) in an extruder at temperatures of up to about 300° C. The masterbatch is then blended with additional polymer (e.g. PET) pellets and melt processed, again at temperatures of up to about 300° C. to form fibers. Accordingly, typical fiber processing conditions would expose the antimicrobial agent to two heating cycles—the first heating cycle in preparing the masterbatch, and the second heating cycle during fiber spinning. In contrast, the process of the present invention avoids the first heat cycle (in preparing the masterbatch), and thus decreases degradation of the antimicrobial agent, particularly antimicrobial agents such as thermally sensitive silver salts.

The methods of the present invention incorporate a master batch approach, in which the masterbatch has greater than about a 4% loading of the silver salt of formula $Ag_aX_bY_cZ_d$, and in particular a loading of between about 4% and about 25% and more particularly a loading of about 9 to about 14% of the silver salt of formula $Ag_aX_bY_cZ_d$. Importantly, the particles of silver salt used in the inventive manufacturing process should be between about 800 nanometers and about 20 micrometers in size, and preferably should have a size distribution of about 1 to about 10 micrometers with a median of about 5 microns. Commercially available silver sulfate is ground and sieved, using techniques familiar to one skilled in the art to provide silver salt particles of this size. A typical particle size distribution of silver sulfate particles used in the present invention, and in the preparation of the Examples described herein is shown in FIG. 1.

The compounding agent can include one or more of the materials described herein. For example the compounding agent can comprise a mixture of a polydimethylsiloxane, a hydroxyl terminated polydimethylsiloxane, an amorphous silica. Alternatively, the compounding agent can comprise a mixture of aliphatic petroleum distillates.

The silver salt particles of the defined size are adhered to the surface of the polymer (e.g., PET) pellets in an even manner covering about 10 to about 90% of the surface of individual pellets, using a mixture of the compounding agents listed herein. The polymer pellets can have any of a variety of shapes, including round, cubic, or cylindrical, and have either smooth surfaces or irregular surfaces. This "compounded master batch" can be described by the following formula: $[Ag_aX_bY_c Z_d (w_1\%)/Cu_aX_bY_cZ_d (wt_2\%)/$Compounding Agent $(wt_3\%)/PET(wt_4\%)]$, wherein the sum of the weight percents is 100%, and the weight percent of the $Ag_aX_bY_c Z_d$ is about 1% to about 26% and the weight percent of the $Cu_aX_bY_cZ_d$ is about 0.1% to about 26% and the weight % of the compounding agent is about 0.15 to about 3%, and the PET makes up the difference.

The compounded master batch is prepared by combining freshly dried polymer (e.g. PET) with the compounding agent (e.g., a mixture of polydimethylsiloxane, hydroxyl terminated polydimethylsiloxane, and amorphous silica) and mixing the combination thoroughly such that the compounding agent evenly covers the surface of the polymer pellets, and forms a viscous mass of polymer pellets. In particular embodiments, the polymer pellets are freshly dried (e.g., in a drying tower), and more particularly freshly dried at temperature between about 70 to about 90° C. Once the pellets are covered with compounding agent and have formed a viscous mass of pellets, a mixture of the appropriate amount of $Ag_aX_bY_c Z_d$ powder and $Cu_aX_bY_cZ_d$ powder are mixed together and then added to the pellets covered with the compounding agent. Alternatively the $Cu_aX_bY_cZ_d$ powder is added first and then the $Ag_aX_bY_c Z_d$ is added, or alternatively the $Ag_aX_bY_c Z_d$ powder is added first and then the $Cu_aX_bY_cZ_d$ powder is added. This combination of polymer pellets, compounding agents and $Ag_aX_bY, Z_d$ and $Cu_aX_bY_cZ_d$ powders are mixed until a free flowing mass of coated polymer pellets is obtained, which is hereinafter referred to as a "compounded master batch." The compounded master batch prepared in the described manner, is subsequently mixed with freshly dried base polymer (e.g., PET if the masterbatch comprises a coated PET pellets), and optionally a master batch of titanium dioxide and a master batch optical brightener such as OB1 from Dalton Clariant, or another optical brightener familiar to one skilled in the art of making fiber. The mixing of the compounded master batch and other master batches can be carried out at ambient temperature and humidity, to form a "letdown polymer." The letdown polymer is melt spun using conventional methods to provide antimicrobial fibers according to the present invention. The extrusion process (e.g. melt spinning) itself requires that the temperature of the letdown polymer mixture is sufficiently high such that it forms a melt. For PET-based compositions according to the present invention, an extruder temperature of about 285° C. to about 305° C., more particularly about 295° C. is used. The melting step may be a separate step in, or it may be part of the extruding process. When the mixture forms a melt at a sufficiently high temperature, it may be extruded using conventional melt spinning devices such as a spinneret. The resulting fiber may then be drawn, crimped, cut and spun into a yarn or other fabric depending on the intended end use, and using techniques that are familiar to one skilled in the art of fiber production. Alternatively the fiber can be extruded in a continuous filament process.

In various embodiments, the order in which the various components of the masterbatch are mixed together can affect the overall process. As discussed herein above, adding the compounding agent first to the polymer pellets, and distributing the compounding agent uniformly over the polymer pellets before adding the powdered antimicrobial agents provides a free flowing mass of coated polymer pellets which are easily processed in conventional melt spinning equipment. Alternative process conditions, such as that disclosed in US 2009/0068286, in which the powdered additives are mixed with the compounding agent first, to form a paste, and then mixed with the polymer pellets, causes agglomerates that are trapped by the melt filters present in the fiber spinning process. As a result, such processes are more difficult to run, and the trapping of agglomerates can reduce the overall percentage of antimicrobial additives ultimately present in the melt spun fibers.

Without being restricted to any particular mechanism, the present inventors have found that amorphous silica is a particularly efficacious component of the compounding agent, as it acts as a desiccant and tends to absorb moisture. This is particularly useful in polyester-based (e.g. PET) compositions and fibers, as it tends to reduce hydrolysis of the polyester.

The fiber produced as described herein, having a composition of $Ag_aX_bY_c Z_d$ (about 0.1 to about 0.50%)+$Cu_aX_bY_c Z_d$ (about 0.01 to about 0.08%)+$NaIO_4$ (about 0.002 to about 0.025%)+Compounding agent (about 0.01 to about 0.1%)+$TiO_2$ (about 0.03 to about 0.6%)+OB1 (about 0.01 to about 0.05%)+PET (about 99.84% to about 98.645%) can be analyzed by ICP-OES (induction coupled-optical emission spectroscopy), ICP-MS (induction coupled mass spectroscopy) or AA (atomic absorbance) to confirm the overall levels of silver and copper in the fiber. These methods, familiar to one skilled in the art, all involve processing the fiber either by combustion or digestion converting and heating the residue to form a plasma, and quantifying the elements present in the plasma. Representative ICP-OES data is reported in the examples provided herein, and in general confirm the levels of silver and copper expected from calculations.

The fiber may also be investigated using standard fiber analysis techniques such as Favimat analysis which measures fiber physical characteristics. Favimat analysis is familiar to those skilled in the art of textile fiber analysis, and involves measurement of multiple fiber properties on multiple fibers and statistically averaging the results including, elongation up to the rupture point, the force required to rupture the fiber, time to rupture, and linear density. The physical measurements are used to calculate fiber properties such as tenacity and modulus. Favimat analysis data is reported in the Examples and confirms that the fibers produced in the embodiments above have Favimat analysis data consistent with fibers that can be used in textile production.

In a particular embodiment, PET fibers of the present invention, prepared as described herein, produce Favimat data substantially similar to that presented in Table 1 and in the Examples.

TABLE 1

Favimat Analysis Data

| Property | Early Stage | SD | Example 1 | SD | Example 15 | SD | PET fiber | SD |
|---|---|---|---|---|---|---|---|---|
| Elongation | 43.19% | 35 | 107.39% | 35 | 41.35% | 15.48 | 43.16% | 20.6 |
| Force | 5.37 g | 0.85 | 6.03 g | 0.85 | 10.50 g | 1.46 | 6.58 g | 1.21 |
| Work to rupture | 2.71 g * cm | 2.51 | 8.54 g * cm | 2.51 | 4.86 g * cm | 2.37 | 3.19 g * cm | 1.91 |
| Tenacity | 2.60 g/den | 0.50 | 2.79 g/den | 0.50 | 5.21 g/den | 0.77 | 3.25 g/den | 1.15 |
| Linear Density | 2.21 den | 0.43 | 2.22 den | 0.43 | 2.06 den | 0.40 | 2.17 den | 0.53 |
| Time to Rupture | 26.2 sec | | 64.71 sec | | 25.26 sec | | 26.17 sec | |
| Modulus | 18.08 g/den | 6.84 | 20.07 g/den | 6.84 | 29.11 g/den | 5.72 | 19.68 g/den | 7.97 |

Fibers present invention, for example having the composition of Formula I may also be analyzed by intrinsic viscosity which is an indirect measure of polymer molecular weight in the fiber. Additives can cause significant polymer cleavage during the melting and extruding processes which would lead to a weaker fiber not appropriate for textile production. Intrinsic viscosity measurements, which are familiar to those skilled in the art of textile fiber manufacture, can be used to identify fibers comprising polymer with high molecular weight. Intrinsic viscosity measurements involve dissolving the polymeric fiber in an appropriate solvent such as (for PET) a mixture of phenol and tetrachloroethane, at a defined concentration such as 0.5 g/dL, at a defined temperature such as 30° C., and measuring the viscosity of the resulting solution generally using a capillary method. Intrinsic viscosity measurement data is reported in the Examples and in Table 2 and is consistent with fiber of suitable quality for use in textile manufacture. In particular embodiments, fibers of the present invention (e.g., of Formula I), prepared by the methods of the present invention, have intrinsic viscosity characteristics substantially similar to that presented in Table 2 and in the Examples.

TABLE 2

Intrinsic Viscosity Measurements on PET Fiber
using Phenol/Tetrachloroethane (60/40 w/w),
30° C., at a concentration of 0.5 g/dL

| Example | IV +/− 0.02 (dL/g) |
|---|---|
| 1 091812F1 | 0.492 |
| 5 112712A | 0.583 |
| 10 022113F | 0.489 |
| 11 022113D | 0.500 |
| 12 022113G | 0.500 |
| 13 022112H | 0.493 |
| 14 022113I | 0.506 |
| 15 030613A | 0.623 |
| PET 022113A | 0.494 |

Fibers of the present invention (e.g. of Formula I) may also be analyzed by differential scanning calorimetry (DSC) which is widely used for examining the thermal transitions of polymeric materials. Melting points ($T_m$) and glass transition temperatures ($T_g$) of conventional polymers are available from standard compilations familiar to those skilled in the art, and can be used to show polymer degradation by the lowering of the melting temperature ($T_m$), since polymer molecular weight can correlate with melting temperature. The degree of crystallinity of a polymer can be estimated from the crystallization temperature ($T_c$) when compared to reference samples. DSC data on PET fibers of Formula I were obtained on a DSC Q1000 v9.9 instrument using a 10° C. to 325° C. temperature range and are reported in the Examples. The DSC of a sample of drawn and heat set PET fiber with only $TiO_2$ and the optical brightener as additives is compared to the DSC of a drawn and heat set PET fiber of the present invention (e.g., of Formula I) and undrawn amorphous polyester, in FIGS. 2a, 2b and 2c. From this data it can be seen that the melting point ($T_m$) of the polymer in fibers prepared according to the present invention is not lower than that of base polymer with just $TiO_2$ and optical brightener after heat setting and drawing. In addition, it can be seen by comparison to the amorphous PET that the glass transition ($T_g$) and the crystallization ($T_c$) of fibers of Formula I has been mostly eliminated by the drawing and heat setting process, as would be expected. Fibers of Formula I, prepared by the methods of the present invention, have DSC characteristics substantially similar to that presented in FIG. 2a.

Because the fibers of the present invention experience less heating compared to fibers produced by conventional melt spinning processes (e.g., the masterbatch compositions provided by the inventive process do not require melt processing), the polymer component of the fibers and polymer compositions of the present invention exhibit less degradation, for example as determined by measuring the molecular weight of the polymer or intrinsic viscosity of the polymer both before and after the melt spinning process. Typically, after melt spinning, the molecular weight or intrinsic viscosity of the polymer component of the fibers of the present invention, prepared by the inventive process, differ from the molecular weight or intrinsic viscosity characteristics of the polymer prior to melt spinning, by less than about 10%. For example, the intrinsic viscosity or molecular weight of the polymer component differs by less than about 1%, about 2%, about 3%, about 4%, about 5%, about 6%, about 7%, about 8%, about 9%, or about 10%, inclusive of all ranges and subranges therebetween.

Fibers of the present invention (e.g. of Formula I) may also be analyzed by backscatter detection on a scanning electron microscope (SEM). SEM images of the fibers of Formula I produced as described herein, show the distribution of silver sulfate particles on or near the fiber surface. Backscatter detection allows elements with a higher atomic number to show up brighter than particles with a lower atomic number (i.e. silver (Ag) with an atomic number of 47 will show up brighter than carbon (C) with an atomic number of 6). Multiple fiber samples were examined by SEM and backscatter SEM. SEM data for fibers of Example 14 in the Examples section, including the normal SEM image and the backscatter SEM image are shown in FIG. 3. Particles of silver sulfate on or just under the surface are easily seen with backscatter detection. These data demonstrate that the process of the present invention successfully delivers small particles of silver salts into the polymeric matrix of the PET fiber. In addition the observed silver sulfate particle sizes appear consistent with the size of the particles added (1-10 microns) and the distribution of the silver sulfate particles in the fiber appears consistent with amount of silver sulfate added, about 0.36 w % for fiber from Example 14. In a particular embodiment, fibers of Formula I of the present invention, prepared by the methods of the present invention, produce backscatter SEM data substantially similar to that presented in FIG. 3.

Fibers of the present invention (e.g. of Formula I) may also be analyzed by electron dispersive x-ray analysis (EDX). EDX can quantify different metals such as silver and lower molecular weight elements such as sulfur. It is a semi-quantitative method that can provide useful information on the relative amounts of different elements. EDX does not give direct information on the oxidation state or salt form of a metal, and is not very sensitive to elements present at 0.2 wt % or less. However, in the case of fibers of Example 14, since the PET base polymer does not contain sulfur, indirect evidence for the existence of silver sulfate can be determined from the observed ratio of silver to sulfur. Fibers of Example 14 were laid down longitudinally for EDX analysis. A bulk or low magnification spectrum detects very little silver (Ag). However, analyzing the individual particles (spot spectrum) easily detected the presence of silver (Ag). For fibers of Example 14, an EDX spot spectrum (an isolated silver particle) is shown in FIG. 4. Gold was used in sample prep as a conductive coating, and is observed in both EDX spectrum, but is not included in the semi-quantitative information. The w/w ratio of silver and sulfur for $Ag_2SO_4$ is calculated to be 6.7, while the observed silver to sulfur ratio is 6.4, supporting the presence of this salt form of silver in the fiber of Example 14. In a particular embodiment, fibers of Formula I of the present invention, prepared by the methods of the present invention, produce EDX data substantially similar to that presented in FIG. 4.

FIG. 5 shows another exemplary SEM image (left) and backscatter detection SEM image (right) of a polyester fiber according to the present invention with antimicrobial silver salt (silver sulfate) particles incorporated in the fibers. The fibers have a diameter of approximately 15 microns, and the silver salt particles have a particle size of about 1-10 microns. The silver salt loading is <1%.

As described above with respect to FIG. 3, the bright spots on the right image of FIG. 5 correspond to silver salt particles that are on or near the surface. Notably, very few of the silver salt particles are on or near the surface.

FIG. 6 shows an SEM backscatter image of cut polyester fibers according to the present invention. This cross-sectional image shows the location of silver salt particles as bright spots. This figure shows silver salt particles in the interior of the fibers, and is further evidence that the silver salt particles are incorporated into the fibers, and not merely coated on the fiber exterior.

FIG. 7 shows an EDX analysis of an SEM image of cut polyester fibers according to the present invention. EDX is an art-recognized method of determining the identity of an element. The red line and yellow arrow were added to the image to show the area that was analyzed by EDX. The green peak, which was also added, indicates the presence of silver in the area analyzed. Thus, EDX analysis also confirms that silver is incorporated into the interior of the fibers of the present invention.

The fiber compositions of Table 2 were tested for their antibacterial properties against E. coli. The results of those tests are presented in FIG. 8. The results for sample 22113A, which does not include silver particles, are included in FIG. 8 for comparison. FIG. 8 shows that all of the fibers tested, other than the control fiber, (i.e., all of the fibers according to the present invention) display antimicrobial activity against E. coli.

Fibers, such as polyester fibers, containing the antimicrobial metal particles as disclosed herein, can be converted into fabric by a variety of methods, including any method known in the art. A person of skill in the art will recognize that the particular method will vary depending on parameters known in the art, including the types of articles to be constructed from the fabric, the intended use of the fabric or articles constructed from the fabric, the particular microbes of concern, and other factors known to or readily determinable by a person of ordinary skill in the art. An exemplary method of converting fiber to fabric is illustrated in the flow diagram of FIG. 9.

The fiber can be produced, for example according to methods described herein, at any suitable fiber production facility. One such suitable production facility is Palmetto Synthetics. The fiber can then be knitted into fabric samples by any acceptable knitting method, such as those that are known to a person of ordinary skill in the textile industry. Knitting can be performed at a suitable knitting facility, which may be the same or different as the fiber production facility. One suitable knitting facility is at Gaston College Textile Technology Center. The fabric samples can then be tested for antimicrobial activity.

For production into commercial articles, the fabric can be stored in a suitable warehouse before spinning the fiber into yarn. Spinning fiber into yarn can be accomplished by any method, such as methods that are known in the textile arts, at any suitable spinning facility. One suitable spinning facility is operated by Beal Manufacturing; another suitable spinning facility is operated by Pharr Yarns, Inc. Once spun, the yarn can be produced into fabric of appropriate shapes or sizes, for example, by weavers using art recognized weaving methods. Alternatively, non-wovens can be produced using art-recognized methods.

Fabric can then be finished at an appropriate finishing facility. Finishing can comprise, for example, washing the fabric to remove weaving lubricants. Depending on the type of articles to be constructed from the fabric and the intended use of such articles, additional finishing steps can also be carried out. Such additional finishing steps can include, for example, one or more of adding softener, adding permanent press, and adding fire retardant.

After finishing, the fabric can be shipped to an appropriate fabricator and manufactured into finished products, such as fabric articles. Exemplary fabric articles include uniforms, including medical such as nurse uniforms, physician uniforms, surgical operating attire, military uniforms, and laboratory coats, consumer articles, such as those commonly used in medical facilities, for example bed pads, bed sheets, pillow cases, drapes, blankets, window curtains, privacy curtains, hospital gowns, face masks, disposable underwear, and textile or gauze bandages or wound coverings, as well as other types of fabric articles where antimicrobial properties may be useful.

Some of the finished products can be tested for antimicrobial activity, for example, as a quality control measure. Finished products can then be transported to, for example, one or more of a warehouse, a wholesaler, a retailer, a customer, or an end user.

Fabric privacy curtains made with antimicrobial fibers were tested after dry cleaning to determine whether the articles retain their antimicrobial properties. A control (not dry cleaned) and negative control (no silver particles) were also tested for comparison. The results are shown in FIG. 10.

As shown in FIG. 10, the dry cleaned curtains retain essentially all of their antimicrobial activity after dry cleaning. Importantly, this result is consistent with experiments showing that the silver particles are incorporated into the fabric, rather than merely coated on the surface. Silver particles coated on the surface of fibers could wash off during dry-cleaning, which can significantly decrease the antimicrobial activity of the fabric. However, silver particles that are incorporated in the fabric's fibers are not easily washed off, therefore, the antimicrobial activity is retained after dry cleaning.

In another embodiment, the methods of the claimed invention provide fibers with an off-white color. Fabrics comprising fibers of the claimed invention have limited color and can be described as substantially white or off-white.

The fiber and the fabrics of the present invention are being surprisingly able to kill microbes deposited on the surface of the fiber or resulting fabric. The fabrics and fibers of the present invention are surprisingly active against gram negative or gram positive bacteria.

The fiber and the fabrics of the present invention are surprisingly able to kill microbes deposited on the surface of the fiber or resulting fabric, including those that are resistant to multiple known antimicrobial agents. These resistant bacterial strains include, for example KPC producing *Klebsiella pneumonia*, Methicillin Resistant *Staph aureus*, Vancomycin Resistant *Enterococcus*, MDR *Pseudomonas aeruginosa*, MDR *Acinetobacter*, 3$^{rd}$ Generation Cephalosporin Resistant *E. Cloacae*, and Fluconazole Resistant *Candida albicans*.

Fabric comprising fibers according to the present invention, prepared by the methods of the claimed invention, are surprisingly active against fungal microbes of different types, and especially it is active against fungi associated with athlete's for and especially it is active against the fungus *Trichophyton Mentagrophytes* (*T. menta*) which is an important component of the fungi that make up Athlete's foot infections.

The fabrics and fibers of the present invention can be washed 25 to 100 times using standardized washing procedures such as the AATCC 61 protocol, and maintain the antibacterial and antifungal activity described herein.

EXAMPLES

General Procedure for Preparation of Compounded Master Batch

The compounding agent is weighed out into a metal mixing flask and combined with a calculated amount of freshly dried polymer (e.g. polyester or PET) pellets at a temperature of 60 to 75° C. The mixture is stirred for 5 to 30 minutes, without further heating or moisture protection, and with a sufficiently powerful overhead stirrer or other mixer, until the compounding agent evenly coats the pellets, and there are no clumps of compounding agent surrounded by polymer pellets. The mixture of compounding agent and polymer pellets is a viscous mass at this point, and not free flowing. The silver salt and the copper salt are independently weighed out and combined and mixed until evenly distributed solid mixture is obtained. This mixture is then added in portions to the mixture of polymer pellets and compounding agent with continuous stirring. As the silver and copper salts are added the mixture becomes free flowing. Stirring is continued until all of the salts are adsorbed on the surface of the pellets. The resulting pellets have a thin coating of copper and silver salts covering anywhere from 10 to 90% of the surface of the pellets depending on the amount of compounding agent and salts used. The covered pellets are passed through a metal mesh that removes any clumps of pellets larger than 5 or 6 pellets. The filtered pellets are then passed over a finer mesh that separates any salt particles not attached to the surface of the pellets. The final pellets are stored in a sealed container protected from moisture until ready to be used in a fiber production run.

ICP-OES (Induction Coupled Plasma Optical Emissions Spectroscopy) was obtained at Galbraith Laboratories, Knoxville Tenn. Samples were ashed, then dissolved in acid prior to analysis.

Favimat Analysis was performed at Gaston College Textile Technology Center, using Textechno Favimat analysis equipment.

Intrinsic viscosity measurements were done using American Society for Testing Material (ASTM) D4603-96 method which involves dissolving the polymeric fiber in a mixture of Phenol and tetrachloroethane, at a concentration of 0.5 g/dL, at 30° C., and measuring the viscosity of the resulting solution using the capillary method.

DSC data on fibers of Formula I were obtained on a DSC Q1000 v9.9 instrument using a 10° C. to 325° C. temperature range.

Example 1

091812F1

Using General Method A

Hot (60 to 80° C.) polyester pellets (PET, cylindrical, 5 kilograms) were added to a 25 gal mechanical mixer along with 30 g of a 50% (w/w) master batch of $TiO_2$ in PET, and 25 g of a 5% master batch of Optical brightener (OB 1, Dalton-Clariant). These ingredients were mixed briefly, and 5 mL of a mixture of 98% distillates (petroleum), hydrotreated heavy naphthenic (CAS 64742-52-5) and 2% distillates (petroleum), hydrotreated light petroleum distillates (CAS 64742-47-2) was added and mixing continued for 3 minutes, until the PET pellets were evenly covered. Silver Sulfate (18 g, AgMPX, Eastman Kodak) was weighed out along with 2 g of anhydrous copper sulfate (CAS 7758-98-7), and both were added to the mixture and stirring was continued for an additional five minutes. This free flowing mixture was transferred to the hopper of a Varemac pilot scale extruder, which had been running neat PET pellets at 295° C., with an operating pressure of 500 PSI. The extruder was fitted with a 1500 hole mesh spinneret. After five minutes the fibers exiting the extruder spinneret were observed as opaque, and were collected in eight separate pools of fiber. Collection of the fiber was stopped when the bulk of modified pellets in the hopper had entered the extruder. The eight pools of fiber were combined into one tow of fiber with 12,000 strands, and feed into a pilot scale drawing and crimping machine. The draw rate was about 3.4:1 and the dip bath was set to about 170° C. The product from the drawing and crimping was collected as loops of crimped tow and air dried for 2 hours. This material was then heat set at 270° C. for 20 minutes, allowed to cool to room temperature, and then cut into 1.5 inch lengths of staple fiber. The staple fiber with a calculated weight composition of 0.36% $Ag_2SO_4$, 0.04% $CuSO_4$ and 0.3% $TiO_2$, were characterized as follows.

ICP-OES (Galbraith Laboratories, GLI Procedure ME-70): A sample of 120.54 mg of cut fiber was combusted to leave an inorganic residue, which was dissolved in acid and analyzed by ICP-OES: Total silver (Ag): 2450 ppm, total copper (Cu): 130 ppm, total titanium (Ti): 1870 ppm.

Favimat Fiber Analysis (average of 21 fibers): Elongation: 107.39%; Force: 6.03 g; Tenacity: 2.79 g/den; Linear Density: 2.22 den; time to rupture: 64.71 sec; Modulus 0-3%: 20.07 g/den.

DSC (Galbraith Laboratories) $T_g$: 132° C.; $T_c$: (not observed), MP: 246° C. (onset: 234.3° C./53.1 J/g)

Intrinsic Viscosity (PolyTech Resources): Method: ASTM 4603-96, Solvent: Phenol/Tetrachloroethane (60/40 w/w), Temperature: 30° C., Concentration: 0.5 g/dL, Result: 0.492 dL/g Example 2

091812F1K-UW

The staple fiber from Example 1 was knitted into a 10 cm tube using methods standard textile methods. The knitted fabric was an off-white color and weight composition of 0.36% $Ag_2SO_4$, 0.04% $CuSO_4$ and 0.3% $TiO_2$, was characterized as follows.

ICP-OES (Galbraith Laboratories, GLI Procedure ME-70): A sample of 59.2 mg of cut fiber was combusted to leave an inorganic residue, which was dissolved in acid and analyzed by ICP-OES: Total silver (Ag): 2430 ppm, total copper (Cu): 166 ppm, total titanium (Ti): 1850 ppm.

Example 3

092812A

Using General Method A

Hot (70 to 80° C.) polyester pellets (PET, cylindrical, 20 kilograms) were added to a 25 gal mechanical mixer along with 120 g of a 50% (w/w) master batch of $TiO_2$ in PET, and 100 g of a 5% master batch of Optical brightener (OB1, Dalton-Clariant). These ingredients were mixed briefly, and 20 ml of a mixture of 98% distillates (petroleum), hydrotreated heavy naphthenic (CAS 64742-52-5) and 2% distillates (petroleum), hydrotreated light (CAS 64742-47-2) was added and mixing continued for 3 minutes, until the PET pellets were evenly covered. Silver sulfate (72 g, AgMPX, Eastman Kodak) was weighed out along with 8 g of anhydrous copper sulfate (CAS 7758-98-7), and both were added to the mechanical mixer and stirring was continued for an additional five minutes. This process was repeated twelve times. The individual twelve batches were added to the hopper of a Varemac Extruder, which had been running neat PET pellets at 295° C., with an operating pressure of 500 PSI. The extruder was fitted with a 1500 hole mesh spinneret. After five minutes the fibers coming from the extruder spinneret were observed as opaque. Collection of the fiber was stopped when all twelve batches of coated pellets had entered the extruder. The pools of fiber were combined into one tow of fiber, with 12,000 strands, and was fed into a drawing and crimping machine. The draw rate was about 3.4:1 and the dip bath was set to about 170° C. The product from the drawing and crimping was collected was heat set at 270° C. for 20 minutes, cooled and cut into 1.5 inch pieces of fiber. The staple fiber with a weight composition of 0.36% $Ag_2SO_4$, 0.04% $CuSO_4$ and 0.3% $TiO_2$, was used directly to make fabric.

Example 4

092812AK-UW

The staple fiber from Example 3 was knitted into a 10 cm tube using standard textile procedures. The knitted fabric, with a weight composition of 0.36% $Ag_2SO_4$, 0.04% $CuSO_4$ and 0.3% $TiO_2$, was characterized as follows.

ICP-OES (Galbraith Laboratories, GLI Procedure ME-70): A sample of 255.57 mg of staple fiber was combusted to leave an inorganic residue, which was dissolved in acid and analyzed by ICP-OES: Total silver (Ag): 2270 ppm, total copper (Cu): 87 ppm, total titanium (Ti): 1740 ppm.

Example 5

112712A

Method B

Hot (70 to 80° C.) polyester pellets (PET, cylindrical, 25 kilograms) were added to a 25 gal mechanical mixer along with 270 mL of a mixture of 98% distillates (petroleum), hydrotreated heavy naphthenic (CAS 64742-52-5) and 2% distillates (petroleum), hydrotreated light (CAS 64742-47-2). This mixture was stirred for five minutes until the PET pellets were evenly covered. Silver sulfate (1000 g, AgMPX, Eastman Kodak) was weighed out along with 111 g of anhydrous copper sulfate (CAS 7758-98-7), and both were added to the mechanical mixer and stirring was continued for an additional 20 minutes. The resulting mixture was semi-free flowing. This process was repeated seventeen times. The coated pellets from seventeen batches were combined in the hopper of a manufacturing scale extruder. The weighed hopper was set to feed in at a 9.3% weight loss rate. A second hopper was filled with a 50% (w/w) master batch of $TiO_2$ in PET and was set to feed in at 0.6%. A third hopper was filled with a 5% master batch of Optical brightener (OB1, Dalton-Clariant), and was set to feed in at 0.3%. A fourth hopper was filled with cylindrical PET heated to 80° C. in a polyester drier, and set to a feed rate of 89.8. The extruder temperature was 285 to 315° C. The Novatec Dryer temperature was 260-300° C. A total of ten, 3002 hole spinnerets were used. The pump speed was set to 3.0. The quench air was set to 38-48° C., and a draw ratio of 3.6 was used. A 0.3% L814 finish was applied to the fiber. This process produced 28 cans of 1.5 denier fiber, and a total of 11602 meters of spun tow. This material was then drawn, crimped, using standard textile processing methods. The product from the drawing and crimping was heat set at 270° C. for 20 minutes, cooled and cut into 1.5 inch pieces of fiber in an 88% by weight yield. The staple fiber with a calculated weight composition of 0.36% $Ag_2SO_4$, 0.039% $CuSO_4$ and 0.3% $TiO_2$, were characterized as follows.

ICP-OES (Galbraith Laboratories, GLI Procedure ME-70): A sample of 113.6 mg of staple fiber was combusted to leave an inorganic residue, which was dissolved in acid and analyzed by ICP-OES: Total silver (Ag): 2090 ppm, total copper (Cu): 124 ppm, total titanium (Ti): 1720 ppm.

Favimat Fiber Analysis (average of 24 fibers): Elongation: 38.05%; Force: 8.93 g; Tenacity: 5.12 g/den; Linear Density: 1.77 den; Time to rupture: 23.16 sec; Modulus 0-3%: 29.83 g/den.

DSC (Galbraith Laboratories) $T_g$: 124° C.; $T_c$: (not observed), MP: 241.8° C. (on set: 235.1° C./53.9 J/g)

Intrinsic Viscosity (PolyTech Resources): Method: ASTM 4603-96, Solvent: Phenol/Tetrachloroethane (60/40 w/w), Temperature: 30° C., Concentration: 0.5 g/dL, Result: 0.583 dL/g Example 6

112712K100 (112712A knitted fabric, 112712G-UW))

The staple fiber from Example 5 was knitted into a 10 cm tube using standard textile procedures. The knitted fabric with a calculated weight composition of 0.36% $Ag_2SO_4$, 0.039% $CuSO_4$ and 0.3% $TiO_2$, was characterized as follows.

ICP-OES (Galbraith Laboratories, GLI Procedure ME-70): A sample of 326.39 mg of staple fiber was combusted to leave an inorganic residue, which was dissolved in acid and analyzed by ICP-OES: Total silver (Ag): 2260 ppm, total copper (Cu): 122 ppm, total titanium (Ti): 1590 ppm.

Example 7

112712W100 (112712M100-UW)

The staple fiber from Example 5 was converted into 100% yarn and woven into a 100% active polyester fabric using standard textile processing methods. The woven fabric, with a calculated weight composition of 0.36% $Ag_2SO_4$, 0.039% $CuSO_4$ and 0.3% $TiO_2$, was characterized as follows.

ICP-OES (Galbraith Laboratories, GLI Procedure ME-70): A sample of 109.8 mg of fabric was combusted to leave an inorganic residue, which was dissolved in acid and analyzed by ICP-OES: Total silver (Ag): 2020 ppm, total copper (Cu): 113 ppm, total titanium (Ti): 1590 ppm.

Example 8

112712W75 (112712M75-UW)

The staple fiber from Example 5 was converted into 100% yarn and woven into a 75% active polyester and 25% non-active polyester fabric using standard textile processing methods. The woven fabric, with a calculated weight composition of 0.27% $Ag_2SO_4$, 0.029% $CuSO_4$ and 0.3% $TiO_2$, was characterized as follows.

ICP-OES (Galbraith Laboratories, GLI Procedure ME-70): A sample of 102.4 mg of fabric was combusted to leave an inorganic residue, which was dissolved in acid and analyzed by ICP-OES: Total silver (Ag): 1590 ppm, total copper (Cu): 91.3 ppm, total titanium (Ti): 1640 ppm.

Example 9

022113E #34

Using a general method for preparing a coated master batch (Method C), Hot PET polyester (60 to 80° C.), 360 g, of ⅜ inch cylindrical polyester pellets was combined with 6.6 g of a paste made of 70-90% of polydimethylsiloxane (CAS 63148-62-9), 7-13% dimethylsiloxane, hydroxyl terminated (CAS 70131-67-8) and 5-10% amorphous silica (CAS 7631-86-9). The pellets were stirred with the paste until all the pellets were evenly covered. This provided a viscous mass of pellets. Silver sulfate (66 g, AgMPX, Eastman Kodak), and copper II sulfate (anhydrous, 7.3 g) were combined, and then added to the PET pellets. This mixture was stirred for 5 to 10 minutes until the pellets became free flowing. The pellets were passed over a sieve to remove unattached salts, and 10.5 g were obtained. The weight of the coated master batch was 429 g. Assuming that the collected salt was 90% silver sulfate, this loading of silver sulfate on the PET pellets was 13% (w/w) and the copper sulfate was 1.5% (w/w). To produce fiber, 123 g of the coated master batch described above was combined with 27 g of a 50% master batch of $TiO_2$ in PET, and 23 g of a 0.5% master batch of optical brightener (OB1, Dalton Clariant) and 4322 g of PET polyester pellets, mixed for 5 minutes, then added to a pilot scale extruder as described in Method A. This produced tow fiber that was drawn and heat set as described in Method A. These fibers, with a calculated weight composition of 0.36% $Ag_2SO_4$, 0.04% $CuSO_4$ and 0.3% $TiO_2$ were characterized as follows.

ICP-OES (Galbraith Laboratories, GLI Procedure ME-70): A sample of 106.83 mg of fiber was combusted to leave an inorganic residue, which was dissolved in acid and analyzed by ICP-OES: Total silver (Ag): 1910 ppm, total copper (Cu): 114 ppm, total titanium (Ti): 1910 ppm.

Example 10

022113F #34

The coated master batch described in Example 9 was used to produce the fiber of Example 10 as follows. 170 g of the coated master batch was combined with 27 g of a 50% master batch of $TiO_2$ in PET, and 23 g of a 0.5% master batch of optical brightener (OB1, Dalton Clariant) and 4275 g of PET polyester pellets, mixed for 5 minutes, then added to a pilot scale extruder as described in Method A. This produced tow fiber that was drawn and heat set as described in Method A. These fibers, with a calculated weight composition of 0.50% $Ag_2SO_4$, 0.057% $CuSO_4$ and 0.3% $TiO_2$ were characterized as follows.

Favimat Fiber Analysis (average of 25 fibers): Elongation: 30.63%; Force: 5.48; Tenacity: 3.17 g/den; Linear Density: 1.79 den; Time to rupture: 18.65 sec; Modulus 0-3%: 37.53 g/den.

DSC (Galbraith Laboratories) $T_g$: 92.8° C.; $T_c$: (not observed), MP: 240.7° C. (on set: 227.5° C./44.71 J/g)

Intrinsic Viscosity (PolyTech Resources): Method: ASTM 4603-96, Solvent: Phenol/Tetrachloroethane (60/40 w/w), Temperature: 30° C., Concentration: 0.5 g/dL, Result: 0.489 dL/g Example 11

022113D #22

Using a general method for preparing a coated master batch (Method C), Hot PET polyester (60 to 80° C.), 180 g, of ⅜ inch cylindrical polyester pellets was combined with 2.0 g of a paste made of 70-90% of polydimethylsiloxane (CAS 63148-62-9), 7-13% dimethylsiloxane, hydroxyl terminated (CAS 70131-67-8) and 5-10% amorphous silica (CAS 7631-86-9). The pellets were stirred with the paste until all the pellets were evenly covered. This provided a viscous mass of pellets. Silver sulfate (20 g, AgMPX, Eastman Kodak) was added to the PET pellets. This mixture was stirred for 5 to 10 minutes until the pellets became free flowing. The pellets were passed over a sieve to remove unattached salts. The weight of the coated master batch was 200 g. The loading of silver sulfate on the PET pellets was calculated to be 9.9% (w/w). To produce fiber, 168 g of the coated master batch was combined with 27 g of a 50% master batch of $TiO_2$ in PET, and 23 g of a 0.5% master batch of optical brightener (OB1, Dalton Clariant) and 4277 g of PET polyester pellets, mixed for 5 minutes, then added to a pilot scale extruder as described in Method A. This produced tow fiber that was drawn and heat set as described in Method A. These fibers, with a calculated weight composition of 0.37% $Ag_2SO_4$, no $CuSO_4$ and 0.3% $TiO_2$ were characterized as follows.

Favimat Fiber Analysis (average of 24 fibers): Elongation: 42.77%; Force: 6.41 g; Tenacity: 3.81 g/den; Linear Density: 1.83 den; Time to rupture: 25.9 sec; Modulus 0-3%: 31.44 g/den.

DSC (Galbraith Laboratories) $T_g$: 91.9° C.; $T_c$: (not observed), MP: 240.5° C. (on set: 227.1° C./45.42 J/g)

Intrinsic Viscosity (PolyTech Resources): Method: ASTM 4603-96, Solvent: Phenol/Tetrachloroethane (60/40 w/w), Temperature: 30° C., Concentration: 0.5 g/dL, Result: 0.500 dL/g Example 12

022113G #24

Using a general method for preparing a coated master batch (Method C), Hot PET polyester (60 to 80° C.), 365 g, of ⅜ inch cylindrical polyester pellets was combined with 3.6 g of a paste made of 70-90% of polydimethylsiloxane (CAS 63148-62-9), 7-13% dimethylsiloxane, hydroxyl terminated (CAS 70131-67-8) and 5-10% amorphous silica (CAS 7631-86-9). The pellets were stirred with the paste until all the pellets were evenly covered. This provided a viscous mass of pellets. Silver sulfate (36 g, AgMPX, Eastman Kodak) and copper II sulfate (anhydrous, 4.0 g) were combined, and then added to the PET pellets. This mixture was stirred for 5 to 10 minutes until the pellets became free flowing. The pellets were passed over a sieve to remove unattached salts. The weight of the coated master batch was 398 g. The loading of silver sulfate on the PET pellets was calculated to be 8.8% (w/w) and the loading of copper II sulfate was 0.98%. To produce fiber, 180 g of the coated master batch was combined with 27 g of a 50% master batch of $TiO_2$ in PET, and 5883 g of PET polyester pellets, mixed for 5 minutes, then added to a pilot scale extruder as described in Method A. This produced tow fiber that was drawn and heat set as described in Method A. These fibers, with a calculated weight composition of 0.26% $Ag_2SO_4$, 0.029% $CuSO_4$ and 0.22% $TiO_2$ were characterized as follows.

Favimat Fiber Analysis (average of 24 fibers): Elongation: 61.17%; Force: 5.48 g; Tenacity: 2.56 g/den; Linear Density: 2.17 den; Time to rupture: 36.98 sec; Modulus 0-3%: 17.55 g/den.

DSC (Galbraith Laboratories) $T_g$: 122.3° C.; $T_c$: (not observed), MP: 240.2° C. (on set: 224.8° C./48.97 J/g)

Intrinsic Viscosity (PolyTech Resources): Method: ASTM 4603-96, Solvent: Phenol/Tetrachloroethane (60/40 w/w), Temperature: 30° C., Concentration: 0.5 g/dL, Result: 0.500 dL/g Example 13

022113H #24

The coated master batch described in Example 12 was used to produce the fiber of Example 13 as follows. 180 g of the coated master batch was combined with 23 g of a 0.5% master batch of optical brightener (OB1, Dalton Clariant) and 4295 g of PET polyester pellets, mixed for 5 minutes, then added to a pilot scale extruder as described in Method A. This produced tow fiber that was drawn and heat set as described in Method A. These fibers, with a calculated weight composition of 0.36% $Ag_2SO_4$, 0.04% $CuSO_4$ and no $TiO_2$ were characterized as follows.

Favimat Fiber Analysis (average of 25 fibers): Elongation: 47.79%; Force: 5.50 g; Tenacity: 2.83 g/den; Linear Density: 2.07 den; Time to rupture: 28.97 sec; Modulus 0-3%: 16.52 g/den.

DSC (Galbraith Laboratories) $T_g$: not observed; $T_c$: (128.2), MP: 240.25° C. (on set: 222.76° C./48.04 J/g)

Intrinsic Viscosity (PolyTech Resources): Method: ASTM 4603-96, Solvent: Phenol/Tetrachloroethane (60/40 w/w), Temperature: 30° C., Concentration: 0.5 g/dL, Result: 0.493 dL/g Example 14

022113I #29

Using a general method for preparing a coated master batch (Method C), Hot PET polyester (60 to 80° C.), 2000 g, of ⅜ inch cylindrical polyester pellets was combined in portions with 18 g of a paste made of 70-90% of polydimethylsiloxane (CAS 63148-62-9), 7-13% dimethylsiloxane, hydroxyl terminated (CAS 70131-67-8) and 5-10% amorphous silica (CAS 7631-86-9). The pellets were stirred with the paste until all the pellets were evenly covered. This provided a viscous mass of pellets. Silver sulfate (224.2 g, AgFX, Eastman Kodak) was added in portions to the PET pellets over 20 to 30 minutes. This mixture was stirred until the pellets became free flowing. The pellets were passed over a sieve to remove unattached salts (19.2 g). The weight of the coated master batch was 2223 g. The loading of silver sulfate on the PET pellets was calculated to be 9.2% (w/w). To produce fiber, 177 g of the coated master batch was combined with 27 g of a 50% master batch of $TiO_2$ in PET, and 23 g of a 0.5% master batch of optical brightener (OB1, Dalton Clariant) and 4268 g of PET polyester pellets, mixed for 5 minutes, then added to a pilot scale extruder as described in Method A. This produced tow fiber that was drawn and heat set as described in Method A. These fibers, with a calculated weight composition of 0.36% $Ag_2SO_4$, 0.04% $CuSO_4$ and 0.3% $TiO_2$ were characterized as follows.

Favimat Fiber Analysis (average of 25 fibers): Elongation: 43.19%; Force: 5.37 g; Tenacity: 2.60 g/den; Linear Density: 2.21 den; Time to rupture: 26.20 sec; Modulus 0-3%: 18.08 g/den.

DSC (Galbraith Laboratories) $T_g$: 112.3° C.; $T_c$: (not observed), MP: 241.01° C. (on set: 228.8° C./48.72 J/g)

Intrinsic Viscosity (PolyTech Resources): Method: ASTM 4603-96, Solvent: Phenol/Tetrachloroethane (60/40 w/w), Temperature: 30° C., Concentration: 0.5 g/dL, Result: 0.506 dL/g Example 15

030613A

Hot PET polyester (60 to 80° C.), 2500 g, of ⅜ inch cylindrical polyester pellets was combined with 390 g of a paste made of 70-90% of polydimethylsiloxane (CAS 63148-62-9), 7-13% dimethylsiloxane, hydroxyl terminated (CAS 70131-67-8) and 5-10% amorphous silica (CAS 7631-86-9). The pellets were stirred with the paste for about ten minutes until an evenly distributed, viscous mass of pellets was obtained. This material was added to a 50 gal rotating mixer along with an additional 18.5 kg of hot PET polyester (60 to 80° C., ⅜ inch cylindrical pellets) and stirred for about 15 minutes until the PET pellets were evenly covered and there were few large clumps of pellets. Copper II sulfate (anhydrous, 375 g) was weighed out and added to the rotating mixture in 2 to 3 portions. Silver sulfate (3,250 g, AgMPX, Eastman Kodak) was weighed out and added to the rotating mixer in three portions. Mixing was continued for an additional 20 minutes until a free flowing batch of coated pellets was obtained. The pellets were passed over a sieve to remove large clumps of pellets. This process was repeated five times, each time obtaining about 25 kilograms of the compounded master batch. Unattached salts and large clumps of pellets were recycled into the next batch. After the 5 runs, the pellets were sieved to remove unattached salt particles (22 g) and combined in a storage drum to give 125,055 g of coated pellets. The loading of silver sulfate on the PET pellets was calculated to be 12.9% (w/w).

This compounded master batch of coated pellets was converted into polyester fiber as follows. The coated pellets were added to a hopper of a manufacturing scale extruder. The weighed hopper was set to feed in at a 2.78% weight loss rate. A second hopper was filled with a 50% (w/w) master batch of $TiO_2$ in PET and was set to feed in at 0.6%. A third hopper was filled with a 5% master batch of Optical brightener (OB1, Dalton-Clariant), and was set to feed in at 0.5%. A fourth hopper was filled with cylindrical PET heated to 80° C. in a polyester drier, and set to a feed rate of 96.1%. The extruder temperature was 295° C. The Novatec Dryer temperature was 260-300° C. A total of ten, 3002 hole spinnerets were used. The pump speed was set to 3.0. The quench air was set to 38-48° C., and a draw ratio of 3.6 was used. A 0.3% L814 finish was applied to the fiber. This process produced 28 cans of 1.5 denier fiber, and a total of 11602 meters of spun tow. This material was then drawn, crimped, using standard textile processing methods. The product from the drawing and crimping was heat set at 270° C. for 20 minutes, cooled and cut into 1.5 inch pieces of fiber in an 88% by weight yield. These fibers, with a calculated weight composition of 0.36% $Ag_2SO_4$, 0.04% $CuSO_4$ and 0.3% $TiO_2$ were characterized as follows.

ICP-OES (Galbraith Laboratories, GLI Procedure ME-70): A sample of 108.8 mg of fiber was combusted to leave an inorganic residue, which was dissolved in acid and analyzed by ICP-OES: Total silver (Ag): 2290 ppm, total copper (Cu): 124 ppm, total titanium (Ti): 1650 ppm.

Favimat Fiber Analysis (average of 25 fibers): Elongation: 41.35%; Force: 10.5 g; Tenacity: 5.21 g/den; Linear Density: 2.06 den; Time to rupture: 25.26 sec; Modulus 0-3%: 29.11 g/den.

DSC (Galbraith Laboratories) $T_g$: 104.24° C.; $T_c$: (142.91, 0.67 J/g), MP: 243.4° C. (on set: 239.8° C./52.8 J/g)

Intrinsic Viscosity (PolyTech Resources): Method: ASTM 4603-96, Solvent: Phenol/Tetrachloroethane (60/40 w/w), Temperature: 30° C., Concentration: 0.5 g/dL, Result: 0.623 dL/g Example 16

030612W100 (not in hand)

The staple fiber from Example 15 was converted into 100% yarn and woven into a 100% active polyester fabric using standard textile processing methods. This fabric has a calculated weight composition of 0.36% $Ag_2SO_4$, 0.04% $CuSO_4$ and 0.3% $TiO_2$.

Example 17

030613W75

The staple fiber from Example 15 was converted into 100% yarn and woven into a 75% active polyester and 25% non-active polyester fabric using standard textile processing methods. This fabric has a calculated weight composition of 0.27% $Ag_2SO_4$, 0.029% $CuSO_4$ and 0.3% $TiO_2$.

Example 18

030613W75 ceil blue scrub

The staple fiber from Example 5 was converted into 100% yarn and woven into a fabric with 75% active polyester yarn and 25% tencel yarn, using standard textile processing methods. The blended fabric was dyed ceil blue in a multiple step process standard for dyeing fabrics made of polyester and tencel. This fabric, with a calculated weight composition of 0.27% $Ag_2SO_4$, 0.029% $CuSO_4$ and 0.3% $TiO_2$ was characterized as follows.

ICP-OES (Galbraith Laboratories, GLI Procedure ME-70): A sample of 102.4 mg of fabric was combusted to leave an inorganic residue, which was completely dissolved in acid and analyzed by ICP-OES: Total silver (Ag): 1590 ppm, total copper (Cu): 91.3 ppm, total titanium (Ti): 1640 ppm.

Example 19

112712B 50% Wool

The staple fiber from Example 5 was converted into 100% yarn and woven into a 50% active polyester and 50% wool fabric using standard textile processing methods. This fabric, with a calculated weight composition of 0.18% $Ag_2SO_4$, 0.02% $CuSO_4$ and 0.15% $TiO_2$ was characterized as follows.

ICP-OES (Galbraith Laboratories, GLI Procedure ME-70): A sample of 102.4 mg of fabric was combusted to leave an inorganic residue, which was completely dissolved in acid and analyzed by ICP-OES: Total silver (Ag): 1590 ppm, total copper (Cu): 91.3 ppm, total titanium (Ti): 1640 ppm.

Example 20

112712B 50% Cotton

The staple fiber from Example 5 was converted into 100% yarn and woven into a 50% active polyester and 50% cotton fabric using standard textile processing methods. This fabric, with a calculated weight composition of 0.18% $Ag_2SO_4$, 0.02% $CuSO_4$ and 0.15% $TiO_2$ was characterized as follows.

ICP-OES (Galbraith Laboratories, GLI Procedure ME-70): A sample of 102.4 mg of fabric was combusted to leave an inorganic residue, which was completely dissolved in acid and analyzed by ICP-OES: Total silver (Ag): 1590 ppm, total copper (Cu): 91.3 ppm, total titanium (Ti): 1640 ppm.

Example 21

112712K10 10% PT

The staple fiber from Example 5 was converted into a yarn of 10% active fiber and 90% Thermolite fiber, and knitted into a fabric using standard textile processing methods. This fabric, with a calculated weight composition of 0.036% $Ag_2SO_4$, 0.004% $CuSO_4$ and 0.03% $TiO_2$ was characterized as follows.

ICP-OES (Galbraith Laboratories, GLI Procedure ME-70): A sample of 102.4 mg of fabric was combusted to leave an inorganic residue, which was completely dissolved in acid and analyzed by ICP-OES: Total silver (Ag): 1590 ppm, total copper (Cu): 91.3 ppm, total titanium (Ti): 1640 ppm.

Example 22

PURSDC116-9010

The staple fiber from Example 5 was converted into 100% active yarn, and woven into a fabric of 10% active yarn and 90% Trevica yarn using standard textile processing methods. This fabric, with a calculated weight composition of 0.036% $Ag_2SO_4$, 0.004% $CuSO_4$ and 0.03% $TiO_2$ was characterized as follows.

ICP-OES (Galbraith Laboratories, GLI Procedure ME-70): A sample of 102.4 mg of fabric was combusted to leave an inorganic residue, which was completely dissolved in acid and analyzed by ICP-OES: Total silver (Ag): 1590 ppm, total copper (Cu): 91.3 ppm, total titanium (Ti): 1640 ppm.

ICP-OES (Galbraith Laboratories, GLI Procedure ME-70): A sample of 102.4 mg of fabric was combusted to leave an inorganic residue, which was completely dissolved in acid and analyzed by ICP-OES: Total silver (Ag): 1590 ppm, total copper (Cu): 91.3 ppm, total titanium (Ti): 1640 ppm.

Table 3 Summarizes the calculate composition of the different types of materials in Examples 1-23. A visual assessment of the color of the different fibers and fabrics is also included. The denier of the fibers in Examples 1, 5, and 10-15 is also reported.

TABLE 3

Examples 1-20

| Example | Description | $Ag_2SO_4$ | $CuSO_4$ | $TiO_2$ | Denier | Color |
|---|---|---|---|---|---|---|
| 1 | PET Fiber | 0.36% | 0.04% | 0.30% | 2.22 den | tan |
| 2 | Knit PET Fabric | 0.36% | 0.04% | 0.30% | | tan |
| 3 | PET Fiber | 0.35% | 0.04% | 0.30% | | tan |
| 4 | Knit PET Fabric | 0.35% | 0.04% | 0.30% | | tan |
| 5 | PET Fiber | 0.36% | 0.039% | 0.30% | 1.77 den | tan |
| 6 | Knit PET Fabric | 0.36% | 0.039% | 0.30% | | tan |
| 7 | Woven PET Fabric 100% active yarn | 0.36% | 0.039% | 0.30% | | tan |
| 8 | Woven PET Fabric 75% active yarn | 0.27% | 0.029% | 0.30%* | | Off white |
| 9 | PET Fiber | 0.36% | 0.04% | 0.30% | | Off white |
| 10 | PET Fiber | 0.50% | 0.057% | 0.30% | 1.79 den | Off white |
| 11 | PET Fiber | 0.37% | 0% | 0.30% | 1.83 den | tan |
| 12 | PET Fiber | 0.26% | 0.029% | 0.22% | 2.17 den | Off white |
| 13 | PET Fiber | 0.36% | 0.04% | 0% | 2.07 den | tan |
| 14 | PET Fiber | 0.36% | 0.04% | 0.30% | 2.21 den | Off white |
| 15 | PET Fiber | 0.36% | 0.04% | 0.30% | 2.06 den | Off white |
| 16 | Woven PET Fabric 100% active yarn | 0.36% | 0.04% | 0.30% | | Off white |
| 17 | Woven PET Fabric 75% active yarn 25% polyester | 0.27% | 0.029% | 0.30% | | white |
| 18 | Woven PET Fabric 75% active yarn 25% tencel | 0.27% | 0.029% | 0.30% | | ceil blue |
| 19 | Woven PET Fabric 50% active PET, 50% wool | 0.18% | 0.02% | 0.15% | | white |
| 20 | Woven PET Fabric 50% active PET, 50% cotton | 0.18% | 0.02% | 0.15% | | white |
| 21 | Knitted Fabric Yarn 10% active and 90% Thermolite | 0.036% | 0.004% | 0.03% | | white |
| 22 | Woven Fabric 10% active yarn 90% Trevica yarn | 0.036% | 0.004% | 0.03% | | blue |
| 23 | Woven Fabric 20% active yarn 80% Trevica yarn | 0.072% | 0.008% | 0.06% | | blue |

Example 23

PURSDC116-8020

The staple fiber from Example 5 was converted into 100% active yarn, and woven into a fabric of 20% active yarn and 80% Trevica yarn using standard textile processing methods. This fabric, with a calculated weight composition of 0.072% $Ag_2SO_4$, 0.008% $CuSO_4$ and 0.06% $TiO_2$ was characterized as follows.

Biological Data:

The knitted and woven fabrics were tested against gram negative (*Klebsiella pneumoniae*) or gram positive (*Staphylococcus aureus*) bacteria using the AATCC 100 protocol for testing of antimicrobial fabrics as follows. In a sterile petri dish, circles of fabric measuring 4.8 cm in diameter were inoculated with 1 mL of a solution of $1\times10^5$ to $2\times10^6$ CFU (colony forming units) of gram negative or gram positive bacteria diluted in a solution of 1:20 Tryptic soy broth supplemented with 0.1% Triton X-100 (wetting agent). The petri dish incubated at 36° C. for 24 hours with humidity control. After the incubation period, the fabric samples were agitated in 10 mL neutralizing solution (Dey-Engley broth), to remove the bacteria. The solutions of recovered bacteria were diluted and plated on agar plates, incubated for 24 hours at 37° C., and then the CFUs were counted using standard methods. The final CFU counts were compared to those from similarly treated, time parallel negative control fabric. The results against gram negative (*Klebsiella pneumoniae*) or gram positive (*Staphylococcus aureus*) or gram negative *Escherichia coli* bacteria are presented in Table 4 below. For *S. aureus* either ATCC strain 33592 or 6538 was used, while for *K. pneumonia* ATCC strain 4352 was used.

Fabric was tested against the fungus *T. mentagrophytes* (ATCC 9533) as follows. A one ml volume of dilute *T. mentagrophytes* spore preparation was used to inoculate each control and test replicate, which were 5 cm diameter circles of fabric. Inoculated carriers were sealed and incubated for 96 hours followed by elution of the fungus from the fabric via agitation in 10 ml D/E broth with 10-20 sterile glass beads. Neutralized samples were vortexed for 20-30 seconds and the elutent passed through sterile glass wool. Filtered samples were enumerated via standard dilution and pour plate technique and incubated at room temperature for approximately 96 hours. The results reported below in Table 4 were calculated based on comparison to a 96 hour control (untreated) sample.

Fabric from Example 6 was tested against two resistant strains each of seven different antibiotic resistant bacteria. The resistant strains and the activity of the fabric from Example 6 are reported in Table 5. The activities were determined using the same AATCC 100 based textile antibacterial protocol described above.

TABLE 5

Activity of Fabric from Example 6 Against Drug Resistant Bacteria

| Drug Resistant Bacteria strains | % Inhibition @ | | |
|---|---|---|---|
| | 30 min | 2 h | 24 h |
| KPC producing *Klebsiella pneumonia* | | | |
| 20651.023 | 99.96 | >99.99 | >99.99 |
| 20651.034 | 99.88 | 99.99 | 99.99 |
| Methicillin Resistant *Staph aureus* | | | |
| C-11-43 | >99.97 | >99.98 | >99.99 |
| C-11-14 | 99.82 | >99.99 | >99.99 |
| Vancomycin Resistant *Enterococcus* | | | |
| C-11-9 | 99.21 | >99.91 | >99.99 |
| C-11-31 MDR | 57.14 | >99.89 | >99.99 |

TABLE 4

Antimicrobial Activity of Fabrics Using AATCC 100 Protocol

| Example | Description | K. pneumonia | S. aureus | E. coli | T. menta |
|---|---|---|---|---|---|
| 2 | Knit PET Fabric | | ++ | +++ | +++ |
| 4 | Knit PET Fabric | +++ | ++ | +++ | |
| 6 | Knit PET Fabric | | + | | + |
| 7 | Woven PET Fabric 100% active yarn | | +++ | +++ | |
| 8 | Woven PET Fabric 75% active yarn | | +++ | +++ | |
| 16 | Woven PET Fabric 100% active yarn | | | | |
| 17 | Woven PET Fabric 75% active yarn 25% polyester | | | | |
| 18 | Woven PET Fabric 75% active yarn 25% tencel | | +++ | | |
| 19 | Woven PET Fabric 50% active PET, 50% wool | | | | +++ |
| 20 | Woven PET Fabric 50% active PET, 50% cotton | | | | + |
| 21 | Knitted Fabric Yarn 10% active and 90% thermolite | | +++ | +++ | |
| 22 | Woven Fabric 10% active yarn 90% trevica yarn | | ++ | ++ | |
| 23 | Woven Fabric 20% active yarn 80% trevica yarn | | ++ | ++ | |

+ >99%;

++ >/=99.9%;

+++ >/=99.99%

TABLE 5-continued

Activity of Fabric from Example 6 Against Drug Resistant Bacteria

| Drug Resistant Bacteria strains | % Inhibition @ | | |
|---|---|---|---|
| | 30 min | 2 h | 24 h |
| *Pseudomonas aeruginosa* | | | |
| 03-H-23 | >99.98 | >99.98 | >99.99 |
| 03-C-102 | >99.99 | >99.99 | >99.99 |
| MDR *Acinetobacter* | | | |
| C-11-42 | >99.96 | >99.98 | >99.99 |
| C-11-64 | >99.97 | >99.99 | >99.99 |
| 3rd Generation Cephalosporin Resistant *E. Cloacae* | | | |
| CL-13-1 | >99.99 | >99.99 | >99.99 |
| CL-13-2 | >99.99 | >99.99 | >99.99 |
| Fluconazole Resistant *Candida albicans* | | | |
| 20535.043 | >99.99 | >99.99 | >99.99 |
| 20323.083 | >99.99 | >99.99 | >99.99 |

Alternatively, fiber was examined for its ability to inhibit *E. coli* using an ATP (adenosine triphosphate) detecting technology. Small samples of fiber or fabric were incubated in 1.7-mL centrifuge tubes at room temperature with (*E. coli*, ATCC 11229C) in Luria-Miller broth or 0.9% saline, containing 0.02% Triton X-100. At various times, 0.4 ml of Bactitre Glo reagent (Promega Inc.) were added to stop the incubation and the level of ATP determined in a Luminometer (Promega Inc.) as measured in RLUs (relative light units). RLUs of time=zero control cultures were compared to those obtained during the course of the experiment to determine percent inhibitions. The data is presented in Table 6.

TABLE 6

Antimicrobial Activity of Fiber and Fabrics with *E. coli* in ATP Assay

| Example | Description | Time to 90% Inhibition |
|---|---|---|
| 1 | PET Fiber | 20 min |
| 2 | Knit PET Fabric | 30 min |
| 3 | PET Fiber | 10 min |
| 4 | Knit PET Fabric | 15 min |
| 5 | PET Fiber | 15 min |
| 6 | Knit PET Fabric | 50 min |
| 7 | Woven PET Fabric 100% active yarn | 10 min |
| 8 | Woven PET Fabric 75% active yarn | >50 min |
| 9 | PET Fiber | 50 min |
| 10 | PET Fiber | 30 min |
| 11 | PET Fiber | >50 min |
| 12 | PET Fiber | >50 min |
| 13 | PET Fiber | 50 min |
| 14 | PET Fiber | >50 min |
| 15 | PET Fiber | 30 min |
| 16 | Woven PET Fabric 100% active yarn | 4 min |
| 17 lab coat | Woven PET Fabric 75% active yarn 25% polyester | ND |
| 18 scrub | Woven PET Fabric 75% active yarn 25% tencel | 50 min |
| 19 112712A fiber | Woven PET Fabric 50% active PET, 50% wool | >50 min |
| 20 112712A fiber | Woven PET Fabric 50% active PET, 50% cotton | >50 min |
| 21 | Knitted Fabric Yarn 10% active and 90% Thermolite | 30 min |
| 22 | Woven Fabric 10% active yarn 90% Trevica yarn | Not done |
| 23 | Woven Fabric 20% active yarn 80% Trevica yarn | Not done |

TABLE 7

Expected and calculated silver salt contents.

| Stage | Fabric # | Measured Ag | w/w % silver salt (calculated) | w/w % silver salt (expected) |
|---|---|---|---|---|
| Development Run | 091812F1 (Example 1) | 2,430 ppm | 0.35% | 0.35% |
| Development Run | 092812K (Example 4) | 2,270 ppm | 0.33% | 0.35% |
| Production Run | 112712K (Example 6) | 2,260 ppm | 0.33% | 0.35% |

Table 7 shows the expected and calculated silver salt content of fibers discussed in the specified Examples. Silver content was measured by ICP-OES elemental analysis. The table shows that the silver salt content of the fibers was very close to expected levels.

The activity of antimicrobial fabrics against a variety of microbes was determined by testing fabrics according to the AATCC 100 protocol. In brief, the tested fabrics were inoculated with about $1\times10^5$ CFU/mL of microbe and then incubated under growth conditions. Bacteria were then harvested from the test articles at specified times in neutralizing broth and plated on agar. The agar plates were then incubated and the CFU's counted. The results are shown in Tables 8 and 9.

TABLE 8

Antimicrobial activity of Fabric 092812K

| Bacteria | Bacteria killed 2 hr incubation time | Bacterial killed 24 hr incubation time |
|---|---|---|
| *E. faecalis* | >99.9% | >99.9% |
| *S. aureus* | >99.9% | >99.9% |
| *K. pneumoniae* | 99.999% | 99.999% |
| *A. baumannii* | 97.3% | >99.9% |
| *P. aeruginosa* | >99.9% | 99.999% |
| *E. cloacae* | >99.9% | >99.99% |
| *P. vulgaris* | >99.9% | 99.999% |
| *C. albicans* | >99.9% | 99.999% |
| *E. coli* | >99.9% | >99.9% |

TABLE 9

Antimicrobial activity of Fabric 112712K

| | Bacteria killed | Bacteria killed |
|---|---|---|
| E. faecalis | >99.9% | 99.999% |
| S. aureus | >99.9% | 99.99% |
| K. pneumoniae | >99.9% | 99.999% |
| A. baumannii | >99.99% | >99.9% |
| P. aeruginosa | >99.9% | 99.999% |
| E. cloacae | >99.9% | >99.9% |
| P. vulgaris | >99.9% | 99.999% |
| C. albicans | 99.54% | >99.9% |
| E. coli | >99.9% | >99.9% |

Tables 8 and 9 show that the tested fabrics have significant antimicrobial activity against a range of bacteria including *S. aureus*.

Tables 10 and 11 demonstrate the effect of washing on the silver content and antimicrobial activity of fabrics was tested. The fabrics were washed fifty times according to the AATCC 61 washing protocol. The silver levels and the antimicrobial activity were determined by ICP-OES and the AATCC 100 protocol, respectively, after specified numbers of washings. Titanium dioxide (a white dye) levels were also tested as a control measurement. The results show that the silver content decreased by less than 5% after 50 washings. Further, there was no significant decrease in antimicrobial activity after 50 washings.

TABLE 10

Silver Levels Over 50 Washes

| Number of Washings | White 100% PT Fabric Measured Silver | White 100% PT Fabric Measured Titanium |
|---|---|---|
| 0 | 2310 ppm | 1680 ppm |
| 5 | 2230 ppm | |
| 10 | 2220 ppm | |
| 20 | 2190 ppm | |
| 25 | 2190 ppm | 1660 ppm |
| 30 | 2320 ppm | |
| 40 | 2190 ppm | |
| 50 | 2190 ppm | 1700 ppm |

TABLE 11

Antimicrobial Activity Against S. aureus (ATCC 6538) Over 50 Washings

| Number of Washings | White 100% PT Fabric % Inhibition of MRSA @ 24 h | Blue 75% PT Fabric % Inhibition of MRSA @ 24 h |
|---|---|---|
| 0 | 99.99% | 99.99% |
| 5 | 99.99% | 99.99% |
| 10 | 99.99% | 99.99% |
| 20 | 99.99% | 99.99% |
| 25 | 99.99% | 99.99% |
| 30 | 99.99% | 99.8% |
| 40 | 99.99% | 99.97% |
| 50 | 99.99% | 99.8% |

The activity of antimicrobial fabric 091812F1-UW against *Trichophyton mentagrophytes* (*T. mentagrophytes*), a fungus commonly found in athlete's foot patients. Table 12 shows that the fabric has significant activity against *T. mentagrophytes*. Specifically, the CFU counts decrease by over 99% after 96 hours.

TABLE 12

Antimicrobial activity against T. mentagrophytes

| Microorganism | Test Substance | Time Point | CFU/Swatch | Average CFU/Swatch | % Reduction Compared to Time Zero | % Reduction Compared to Control at 96 Hours |
|---|---|---|---|---|---|---|
| T. mentagrophytes ATCC 9533 | 100% Polyester Black Control | Time Zero | 1.25E+04 1.60E+04 | 1.43E+04 | N/A | |
| | | 96 Hours | 3.50E+06 Inconclusive+ | 3.50E+06 | | |
| | 091812F1-UW | 96 Hours | <50 <50 | <50 | 99.6491% | 99.9986% |

The results in Table 12 are displayed as a bar graph in FIG. 11.

FIG. 12 compares images of a control fabric (left) without antimicrobial silver particles and fabric 091812F1-UW (right) after exposure to *T. mentagrophytes*. Fungus is visible in the control fabric but not on the 091812F1-UW fabric.

Thus, the antimicrobial fabrics have demonstrated antibacterial and anti-fungal activity.

The invention claimed is:

1. A polymer composition comprising:
    (a) a first population of high-melting polymer particles;
    (b) about 1 to about 26 wt.% of a silver salt having the formula $Ag_aX_bY_cZ_d$;
    (c) about 0.1 to about 2.6 wt.% of a copper salt having the formula $Cu_aX_bY_cZ_d$; and
    (d) about 0.15 to about 3 wt.% of a compounding agent;
    Ag is Ag(I) or Ag(II), and a is 1 to 4;
    each X is sulfur, and b is independently 1 to 4;
    each Y is oxygen, and c is independently 2 to 8;
    each Z is independently H; $C_1$-$C_{14}$ alkyl; $C_3$-$C_8$ cycloalkyl; $C_1$-$C_8$ alkyl substituted by $C_3$-$C_6$ cycloalkyl; $C_1$-$C_8$ alkyl optionally substituted by $C_6$-$C_{10}$ aryl; $C_6$-$C_{10}$ aryl; $C_6$-$C_{10}$ aryl substituted by $C_1$-$C_{14}$ alkyl, $C_3$-$C_8$ cycloalkyl, $C_1$-$C_8$ alkyl substituted by $C_3$-$C_6$ cycloalkyl, or halogen;
    d is 0 or 1;
    wherein a mixture of the silver salt, copper salt, and compounding agent is disposed over the surface of the high-melting polymer particles.

2. The polymer composition of claim 1, wherein the high-melting polymer particles comprise a polyethylene terephthalate polymer, Nylon 6, or Nylon 6,6.

3. The polymer composition of claim 1, wherein the compounding agent is one or more compounds selected from the group consisting of polydimethylsiloxane, hydroxyl terminated polydimethylsiloxane, amorphous silica, aliphatic hydrocarbons, aliphatic petroleum distillates, and liquefied petroleum gas.

4. The polymer composition of claim 2, wherein the compounding agent comprises a mixture of polydimethylsiloxane, hydroxyl terminated dimethylsiloxane, and amorphous silica.

5. The polymer composition of claim 1, further comprising a pigment and an optical brightener.

6. The polymer composition of claim 5, wherein the pigment is titanium dioxide.

7. The polymer composition of claim 1, wherein the polymer composition has not been subjected to heating in excess of about 110° C.

8. A polymer mixture comprising the combination of the polymer composition of claim 1 with a second population of high-melting polymer particles, whereby the polymer mixture has the following composition:
   (i) about 0.05 to about 0.50 wt. % silver salt having the formula $Ag_aX_bY_cZ_d$;
   (ii) about 0.01 to about 0.1 wt. % copper salt having the formula $Cu_aX_bY_cZ_d$;
   (iii) about 0.01 to about 0.1 wt. % compounding agent ; and
   (iv) high-melting polymer particles from the first and second populations of high-melting polymer particles.

9. The polymer mixture of claim 8, wherein the high-melting polymer particles from the first and second populations of high-melting polymer particles comprise a polyethylene terephthalate polymer.

10. The polymer mixture of claim 8, further comprising about 0.0002 to about 0.025% $NaIO_4$.

11. The polymer mixture of claim 8, further comprising a pigment and an optical brightener.

12. The polymer mixture of claim 11, wherein the pigment is titanium dioxide.

13. The polymer mixture of claim 8, in the form of a melt spun fiber.

14. The polymer mixture of claim 9, in the form of a melt spun fiber.

15. A method of making the polymer composition of claim 1 comprising coating a mixture of the compounding agent, silver salt, and copper salt over the surface of the high-melting polymer particles.

16. The method of claim 15, wherein the high-melting polymer particles comprise a polyethylene terephthalate polymer.

17. The method of claim 15, wherein said coating comprises:
   (1) coating the first population of high-melting polymer particles with the compounding agent; and
   (2) adding the silver salt and copper salt to the coated high-melting polymer particles, thereby forming a mixture of the silver salt, copper salt, and compounding agent disposed over the surface of the high-melting polymer particles.

18. The method of claim 17, wherein the high-melting polymer particles comprise a polyethylene terephthalate polymer, nylon 6, or nylon 6,6.

19. A method of making the polymer mixture of claim 8, comprising mixing the first population of high-melting polymer particles, having a mixture of compounding agent, silver salt having the formula $Ag_aX_bY_cZ_d$, and copper salt having the formula $Cu_zX_bY_cZ_d$ disposed over the surface thereof, with the second population of high-melting polymer particles.

\* \* \* \* \*